United States Patent
Pamnani et al.

(10) Patent No.: US 9,955,858 B2
(45) Date of Patent: May 1, 2018

(54) SURGICAL INSTRUMENT AND METHOD FOR USE

(75) Inventors: Ravi Pamnani, Belmont, CA (US); Thang Tom Ung, Milpitas, CA (US)

(73) Assignee: MAQUET CARDIOVASCULAR LLC, San Jose, CA (US)

( * ) Notice: Subject to any disclaimer, the term of this patent is extended or adjusted under 35 U.S.C. 154(b) by 902 days.

(21) Appl. No.: 12/545,690

(22) Filed: Aug. 21, 2009

(65) Prior Publication Data
US 2011/0046439 A1    Feb. 24, 2011

(51) Int. Cl.
| A61B 18/18 | (2006.01) |
| A61B 1/018 | (2006.01) |
| A61B 1/12 | (2006.01) |
| A61B 17/00 | (2006.01) |
| A61B 17/29 | (2006.01) |
| A61B 90/00 | (2016.01) |

(52) U.S. Cl.
CPC .............. *A61B 1/018* (2013.01); *A61B 1/126* (2013.01); *A61B 17/00008* (2013.01); *A61B 90/361* (2016.02); *A61B 2017/2922* (2013.01); *A61B 2017/2923* (2013.01); *A61B 2017/2936* (2013.01)

(58) Field of Classification Search
CPC . A61F 2/062; A61F 2/06; A61B 17/29; A61B 2017/2926
USPC ......... 600/157, 36, 104, 568, 205, 235, 201, 600/564, 101; 607/98, 99; 606/28, 29, 606/52, 206, 207, 37, 51, 205, 46, 47, 606/118, 45, 170, 172, 210; 604/118, 604/151, 173, 22
See application file for complete search history.

(56) References Cited

U.S. PATENT DOCUMENTS

| 2,137,710 A | 12/1937 | Anderson |
| 4,031,898 A | 6/1977 | Hiltebrandt |
| 4,071,028 A | 1/1978 | Perkins |
| 4,128,099 A | 12/1978 | Bauer |
| 4,281,646 A | 8/1981 | Kinoshita |
| 4,418,692 A | 12/1983 | Guay |
| 4,468,217 A | 8/1984 | Kuzmick |
| 4,759,362 A | 7/1988 | Taniguchi |
| 4,767,519 A | 8/1988 | de Nora |
| 4,801,015 A | 1/1989 | Lubock |
| 4,884,559 A | 12/1989 | Collins |

(Continued)

FOREIGN PATENT DOCUMENTS

| AU | 2006229913 B2 | 11/2011 |
| CA | 2602015 A1 | 10/2006 |

(Continued)

OTHER PUBLICATIONS

U.S. Appl. No. 13/494,985, filed Jun. 12, 2012.

(Continued)

*Primary Examiner* — Alexandra L Newton

(57) ABSTRACT

An apparatus includes a tubular structure having a proximal end, a distal end, and a body extending between the proximal and distal ends, wherein the body includes a lumen for housing at least a part of an imaging device, and a fluid delivery channel that is fixed in position relative to the body, and an opening that is in fluid communication with the fluid delivery channel, wherein the fluid delivery channel has a first portion, and a second portion that forms an angle with an axis of the first portion.

26 Claims, 17 Drawing Sheets

(56) References Cited

U.S. PATENT DOCUMENTS

| | | | | |
|---|---|---|---|---|
| 5,009,661 | A | 4/1991 | Michelson | |
| 5,052,402 | A * | 10/1991 | Bencini et al. | 600/564 |
| 5,098,430 | A | 3/1992 | Fleenor | |
| 5,108,474 | A | 4/1992 | Riedy | |
| 5,147,356 | A | 9/1992 | Bhatta | |
| 5,151,102 | A | 9/1992 | Kamiyama | |
| 5,154,709 | A | 10/1992 | Johnson | |
| 5,156,613 | A | 10/1992 | Sawyer | |
| 5,160,334 | A | 11/1992 | Billings | |
| 5,217,460 | A | 6/1993 | Knoepfler | |
| 5,258,006 | A | 11/1993 | Rydell | |
| 5,282,799 | A | 2/1994 | Rydell | |
| 5,290,278 | A | 3/1994 | Anderson | |
| 5,300,065 | A | 4/1994 | Anderson | |
| 5,312,426 | A * | 5/1994 | Segawa et al. | 606/158 |
| 5,314,424 | A | 5/1994 | Nicholas | |
| 5,318,040 | A | 6/1994 | Kensey | |
| 5,336,221 | A | 8/1994 | Anderson | |
| 5,342,381 | A | 8/1994 | Tidemand | |
| 5,352,222 | A | 10/1994 | Rydell | |
| 5,356,408 | A | 10/1994 | Rydell | |
| 5,361,583 | A | 11/1994 | Huitema | |
| 5,364,395 | A | 11/1994 | West, Jr. | |
| 5,383,888 | A | 1/1995 | Zvenyatsky | |
| 5,405,344 | A | 4/1995 | Williamson | |
| 5,443,463 | A | 8/1995 | Stern | |
| 5,445,638 | A | 8/1995 | Rydell | |
| 5,451,222 | A | 9/1995 | De Maagd | |
| 5,453,599 | A | 9/1995 | Hall, Jr. | |
| 5,462,546 | A | 10/1995 | Rydell | |
| 5,472,442 | A | 12/1995 | Klicek | |
| 5,496,317 | A | 3/1996 | Goble | |
| 5,507,744 | A | 4/1996 | Tay | |
| 5,507,773 | A | 4/1996 | Huitema | |
| 5,509,922 | A | 4/1996 | Aranyi | |
| 5,514,134 | A | 5/1996 | Rydell | |
| 5,562,503 | A | 10/1996 | Ellman | |
| 5,599,350 | A | 2/1997 | Schulze | |
| 5,624,452 | A | 4/1997 | Yates | |
| 5,647,871 | A * | 7/1997 | Levine et al. | 606/45 |
| 5,669,934 | A | 9/1997 | Sawyer | |
| 5,674,219 | A | 10/1997 | Monson | |
| 5,683,412 | A | 11/1997 | Scarfone | |
| 5,709,675 | A | 1/1998 | Williams | |
| 5,709,680 | A | 1/1998 | Yates | |
| 5,716,366 | A | 2/1998 | Yates | |
| 5,722,962 | A | 3/1998 | Garcia | |
| 5,741,285 | A | 4/1998 | McBrayer | |
| 5,752,973 | A | 5/1998 | Kieturakis | |
| 5,755,717 | A * | 5/1998 | Yates et al. | 606/51 |
| 5,766,134 | A | 6/1998 | Lisak | |
| 5,766,166 | A | 6/1998 | Hooven | |
| 5,776,130 | A | 7/1998 | Buysse | |
| 5,807,393 | A | 9/1998 | Williamson et al. | |
| 5,810,810 | A | 9/1998 | Tay | |
| 5,810,811 | A | 9/1998 | Yates et al. | |
| 5,827,271 | A | 10/1998 | Buysse | |
| 5,833,690 | A | 11/1998 | Yates | |
| 5,843,017 | A | 12/1998 | Yoon | |
| 5,849,011 | A | 12/1998 | Jones | |
| 5,853,410 | A | 12/1998 | Greff | |
| 5,860,975 | A | 1/1999 | Goble | |
| 5,871,496 | A * | 2/1999 | Ginn et al. | 606/190 |
| 5,891,141 | A | 4/1999 | Rydell | |
| 5,906,630 | A | 5/1999 | Anderhub | |
| 5,908,420 | A | 6/1999 | Parins | |
| 5,911,719 | A | 6/1999 | Eggers | |
| 5,944,718 | A | 8/1999 | Austin | |
| 5,947,984 | A | 9/1999 | Whipple | |
| 5,954,686 | A | 9/1999 | Garito | |
| 5,997,533 | A | 12/1999 | Kuhns | |
| 6,004,320 | A | 12/1999 | Casscells et al. | |
| 6,022,313 | A * | 2/2000 | Ginn et al. | 600/114 |
| 6,024,741 | A | 2/2000 | Williamson, IV | |
| 6,027,501 | A | 2/2000 | Goble | |
| 6,033,424 | A | 3/2000 | Ouchi | |
| 6,039,733 | A | 3/2000 | Buysse | |
| 6,059,781 | A | 5/2000 | Yamanashi | |
| 6,066,151 | A | 5/2000 | Miyawaki | |
| 6,074,389 | A * | 6/2000 | Levine et al. | 606/45 |
| 6,110,190 | A * | 8/2000 | Ginn et al. | 606/190 |
| 6,113,596 | A | 9/2000 | Hooven | |
| 6,174,309 | B1 | 1/2001 | Wrublewski | |
| 6,179,837 | B1 | 1/2001 | Hooven | |
| 6,190,386 | B1 | 2/2001 | Rydell | |
| 6,206,876 | B1 * | 3/2001 | Levine et al. | 606/45 |
| 6,254,623 | B1 | 7/2001 | Haibel, Jr. | |
| 6,267,761 | B1 | 7/2001 | Ryan | |
| 6,270,497 | B1 | 8/2001 | Sekino | |
| 6,273,887 | B1 | 8/2001 | Yamauchi | |
| 6,352,503 | B1 * | 3/2002 | Matsui et al. | 600/104 |
| 6,352,532 | B1 | 3/2002 | Kramer | |
| 6,391,029 | B1 | 5/2002 | Hooven | |
| 6,406,454 | B1 | 6/2002 | Hajianpour | |
| 6,432,105 | B1 | 8/2002 | Ellman et al. | |
| 6,458,122 | B1 | 10/2002 | Pozzato | |
| 6,464,701 | B1 | 10/2002 | Hooven | |
| 6,478,794 | B1 | 11/2002 | Trapp | |
| 6,517,536 | B2 | 2/2003 | Hooven | |
| 6,524,307 | B1 | 2/2003 | Palmerton | |
| 6,527,771 | B1 | 3/2003 | Weadock | |
| 6,544,210 | B1 | 4/2003 | Trudel | |
| 6,551,313 | B1 | 4/2003 | Levin | |
| 6,576,033 | B1 | 6/2003 | Booth | |
| 6,582,451 | B1 | 6/2003 | Marucci | |
| 6,582,582 | B2 | 6/2003 | Becking | |
| 6,602,252 | B2 | 8/2003 | Mollenauer | |
| 6,613,069 | B2 | 9/2003 | Boyd | |
| 6,626,901 | B1 | 9/2003 | Treat | |
| 6,652,514 | B2 | 11/2003 | Ellman | |
| 6,656,177 | B2 | 12/2003 | Truckai | |
| 6,663,610 | B1 | 12/2003 | Thompson | |
| 6,682,528 | B2 | 1/2004 | Frazier | |
| 6,685,665 | B2 | 2/2004 | Booth | |
| 6,695,837 | B2 | 2/2004 | Howell | |
| 6,746,504 | B2 | 6/2004 | Booth | |
| 6,770,072 | B1 | 8/2004 | Truckai | |
| 6,773,409 | B2 | 8/2004 | Truckai | |
| 6,802,843 | B2 | 10/2004 | Truckai | |
| 6,821,273 | B2 * | 11/2004 | Mollenauer | 606/28 |
| 6,830,569 | B2 | 12/2004 | Thompson | |
| 6,860,880 | B2 | 3/2005 | Treat | |
| 6,908,463 | B2 | 6/2005 | Treat | |
| 6,958,070 | B2 | 10/2005 | Witt | |
| 6,966,907 | B2 | 11/2005 | Goble | |
| 6,966,909 | B2 | 11/2005 | Marshall | |
| 6,994,707 | B2 | 2/2006 | Ellman | |
| 7,033,356 | B2 | 4/2006 | Latterell | |
| 7,083,620 | B2 | 8/2006 | Jahns et al. | |
| 7,094,231 | B1 | 8/2006 | Ellman | |
| 7,112,199 | B2 | 9/2006 | Cosmescu | |
| 7,147,637 | B2 | 12/2006 | Goble | |
| 7,204,835 | B2 | 4/2007 | Latterell | |
| 7,211,080 | B2 | 5/2007 | Treat | |
| 7,306,599 | B2 | 12/2007 | Karasawa et al. | |
| 7,316,683 | B2 * | 1/2008 | Kasahara et al. | 606/45 |
| 7,326,202 | B2 | 2/2008 | McGaffigan | |
| 7,329,257 | B2 | 2/2008 | Kanehira et al. | |
| 7,364,577 | B2 | 4/2008 | Wham | |
| 7,367,976 | B2 | 5/2008 | Lawes et al. | |
| 7,396,356 | B2 * | 7/2008 | Mollenauer | 606/51 |
| 7,513,896 | B2 | 4/2009 | Orszulak | |
| 7,632,270 | B2 | 12/2009 | Livneh | |
| 7,645,289 | B2 * | 1/2010 | Bayer | 606/159 |
| 7,695,470 | B1 * | 4/2010 | Stewart et al. | 606/51 |
| 7,699,861 | B2 * | 4/2010 | Bayer | 606/159 |
| 7,887,558 | B2 * | 2/2011 | Lin et al. | 606/159 |
| 7,918,845 | B2 * | 4/2011 | Saadat et al. | 606/1 |
| 7,918,848 | B2 | 4/2011 | Lau | |
| 8,197,472 | B2 | 6/2012 | Lau | |
| 8,221,306 | B2 * | 7/2012 | Okada et al. | 600/106 |
| 8,251,989 | B1 | 8/2012 | Newton et al. | |
| 8,257,352 | B2 | 9/2012 | Lawes et al. | |
| 8,425,508 | B2 * | 4/2013 | Kasahara et al. | 606/45 |

(56) References Cited

U.S. PATENT DOCUMENTS

| | | | |
|---|---|---|---|
| 8,623,003 B2 | 1/2014 | Lau et al. | |
| 8,657,818 B2* | 2/2014 | Lin | 606/51 |
| 8,894,638 B2 | 11/2014 | Lau et al. | |
| 8,961,503 B2 | 2/2015 | Lau et al. | |
| 9,402,680 B2 | 8/2016 | Ginnebaugh et al. | |
| 2002/0019631 A1 | 2/2002 | Kidder | |
| 2002/0058938 A1 | 5/2002 | Cosmescu | |
| 2002/0115997 A1* | 8/2002 | Truckai | A61B 18/1445 606/51 |
| 2002/0128603 A1 | 9/2002 | Booth | |
| 2003/0014052 A1 | 1/2003 | Buysse | |
| 2003/0060816 A1 | 3/2003 | Iida | |
| 2003/0073991 A1 | 4/2003 | Francischelli | |
| 2003/0073994 A1 | 4/2003 | Schulze | |
| 2003/0125734 A1* | 7/2003 | Mollenauer | 606/51 |
| 2003/0130654 A1* | 7/2003 | Kasahara et al. | 606/45 |
| 2003/0130674 A1* | 7/2003 | Kasahara et al. | 606/159 |
| 2003/0130675 A1* | 7/2003 | Kasahara et al. | 606/159 |
| 2003/0139649 A1* | 7/2003 | Kasahara et al. | 600/157 |
| 2003/0144652 A1 | 7/2003 | Baker | |
| 2003/0144660 A1* | 7/2003 | Mollenauer | 606/45 |
| 2003/0163123 A1 | 8/2003 | Goble | |
| 2003/0171747 A1 | 9/2003 | Kanehira | |
| 2003/0187429 A1 | 10/2003 | Karasawa | |
| 2004/0054365 A1 | 3/2004 | Goble | |
| 2004/0064151 A1 | 4/2004 | Mollenauer | |
| 2004/0078035 A1 | 4/2004 | Kanehira | |
| 2004/0102450 A1 | 5/2004 | Ewing et al. | |
| 2004/0133228 A1* | 7/2004 | Bayer | 606/190 |
| 2004/0176756 A1 | 9/2004 | McGaffigan | |
| 2004/0204725 A1* | 10/2004 | Bayer | 606/159 |
| 2004/0260279 A1 | 12/2004 | Goble | |
| 2005/0033278 A1* | 2/2005 | McClurken et al. | 606/41 |
| 2005/0049633 A1* | 3/2005 | Watanabe | 606/205 |
| 2005/0072827 A1* | 4/2005 | Mollenauer | 227/180.1 |
| 2005/0113826 A1 | 5/2005 | Johnson | |
| 2005/0113828 A1 | 5/2005 | Shields et al. | |
| 2005/0171533 A1 | 8/2005 | Latterell | |
| 2006/0041254 A1 | 2/2006 | Francischelli et al. | |
| 2006/0074444 A1* | 4/2006 | Lin et al. | 606/190 |
| 2006/0211916 A1* | 9/2006 | Kasahara et al. | 600/114 |
| 2006/0217697 A1* | 9/2006 | Lau et al. | 606/29 |
| 2006/0217706 A1* | 9/2006 | Lau et al. | 606/45 |
| 2006/0235379 A1* | 10/2006 | McClurken et al. | 606/45 |
| 2006/0271037 A1 | 11/2006 | Maroney et al. | |
| 2007/0021405 A1 | 1/2007 | Abouabdellah et al. | |
| 2007/0021424 A1 | 1/2007 | Abouabdellah et al. | |
| 2007/0027141 A1 | 2/2007 | Abouabdellah et al. | |
| 2007/0078456 A1 | 4/2007 | Dumbauld et al. | |
| 2007/0149993 A1* | 6/2007 | Kasahara et al. | 606/190 |
| 2007/0173814 A1 | 7/2007 | Hixson et al. | |
| 2007/0213749 A1* | 9/2007 | Kogasaka et al. | 606/153 |
| 2007/0260242 A1 | 11/2007 | Dycus | |
| 2007/0293856 A1 | 12/2007 | Paul | |
| 2007/0293858 A1 | 12/2007 | Fischer | |
| 2008/0015567 A1* | 1/2008 | Kimura | 606/41 |
| 2008/0015575 A1 | 1/2008 | Odom | |
| 2008/0039835 A1* | 2/2008 | Johnson | A61B 18/1442 606/48 |
| 2008/0154091 A1* | 6/2008 | Dejima et al. | 600/104 |
| 2008/0306335 A1* | 12/2008 | Lau et al. | 600/106 |
| 2009/0024121 A1* | 1/2009 | Kasahara et al. | 606/39 |
| 2009/0118730 A1* | 5/2009 | Mollenauer | 606/48 |
| 2009/0299367 A1* | 12/2009 | Ginnebaugh et al. | 606/51 |
| 2010/0048992 A1* | 2/2010 | Okada et al. | 600/106 |
| 2010/0292533 A1* | 11/2010 | Kasahara et al. | 600/104 |
| 2011/0046439 A1 | 2/2011 | Pamnani et al. | |
| 2011/0046624 A1* | 2/2011 | Lin | 606/51 |
| 2011/0257643 A1 | 10/2011 | Lau | |
| 2011/0288369 A1 | 11/2011 | Ginnebaugh | |
| 2011/0288546 A1 | 11/2011 | Abbott | |
| 2012/0283720 A1 | 11/2012 | Newton et al. | |
| 2012/0316550 A1 | 12/2012 | Ullrich, Jr. et al. | |
| 2013/0018373 A1 | 1/2013 | Lau et al. | |
| 2014/0194876 A1 | 7/2014 | Lau et al. | |

FOREIGN PATENT DOCUMENTS

| | | |
|---|---|---|
| CA | 2602381 A1 | 10/2006 |
| DE | 10328514 B3 | 3/2005 |
| EP | 538984 A2 | 4/1993 |
| EP | 538984 A3 | 7/1993 |
| EP | 538984 B1 | 3/1997 |
| EP | 1330991 A1 | 7/2003 |
| EP | 1632192 A1 | 3/2006 |
| EP | 1330991 B1 | 9/2007 |
| EP | 1878399 A1 | 1/2008 |
| EP | 1894535 A2 | 3/2008 |
| EP | 1632192 B1 | 3/2009 |
| EP | 2106762 A1 | 10/2009 |
| EP | 1885270 B1 | 8/2010 |
| EP | 1861034 B1 | 9/2010 |
| EP | 2285305 A2 | 2/2011 |
| EP | 1894535 A3 | 3/2011 |
| JP | H07508666 A | 9/1995 |
| JP | H10511030 A | 10/1998 |
| JP | 2000135222 A | 5/2000 |
| JP | 2000139943 A | 5/2000 |
| JP | 2003144451 A | 5/2003 |
| JP | 2005058553 A | 3/2005 |
| JP | 2005514102 A | 5/2005 |
| JP | 2008534068 A | 8/2008 |
| JP | 2008534069 A | 8/2008 |
| JP | 2011521723 A | 7/2011 |
| JP | 4966959 B2 | 7/2012 |
| WO | 1993020769 A1 | 10/1993 |
| WO | 9705829 A1 | 2/1997 |
| WO | 9710764 A1 | 3/1997 |
| WO | 0047124 A1 | 8/2000 |
| WO | 02080794 A1 | 10/2002 |
| WO | 03057058 A1 | 7/2003 |
| WO | 03061456 A2 | 7/2003 |
| WO | 2003061456 A3 | 1/2004 |
| WO | 2005048863 A1 | 6/2005 |
| WO | 2006104835 A1 | 10/2006 |
| WO | 2006104836 A2 | 10/2006 |
| WO | 2006104836 A3 | 1/2007 |
| WO | 2009039179 A1 | 3/2009 |
| WO | 2009154976 A2 | 12/2009 |
| WO | 2009154976 A3 | 3/2010 |
| WO | 2009154976 A4 | 5/2010 |
| WO | 2009154976 A9 | 2/2011 |

OTHER PUBLICATIONS

U.S. Appl. No. 13/549,367, filed Jul. 13, 2012.
Stedman's Medical Dictionary, pp. 3 and 238 (1982), Waverly Press, Inc.
International Search Report and Written Opinion dated Jan. 19, 2010 for PCT Application No. PCT/US2009/045272; (20 pages).
Non-Final Office Action dated May 7, 2012 for U.S. Appl. No. 12/472,657; (22 pages).
U.S. Appl. No. 13/094,783, filed Apr. 26, 2011.
PCT International Search Report and Written Opinion, PCT/US2006/010569, dated Jul 24, 2006, 20 pages.
PCT International Preliminary Report on Patentability, PCT/US2006/010569, dated Sep. 25, 2007, 9 pages.
PCT International Search Report and Written Opinion, PCT/US2006/010568, dated Jul. 24, 2006, 8 pages.
PCT International Preliminary Report on Patentability, PCT/US2006/010568, dated Sep. 25, 2007, 6 pages.
European Examination Report, EP 06739388.4, dated Sep. 17, 2008, 7 pages.
Non-Final Office Action dated Mar. 14, 2012 for U.S. Appl. No. 13/094,783; (8 pages).
European Examination Report, EP Application No. EP 06739387.6, dated Dec. 11, 2008 (4 pages).
U.S. Appl. No. 13/047,778, filed Mar. 14, 2011.
U.S. Appl. No. 14/148,671, filed Jan. 6, 2014.
U.S. Appl. No. 12/472,657, filed May 27, 2009.

* cited by examiner

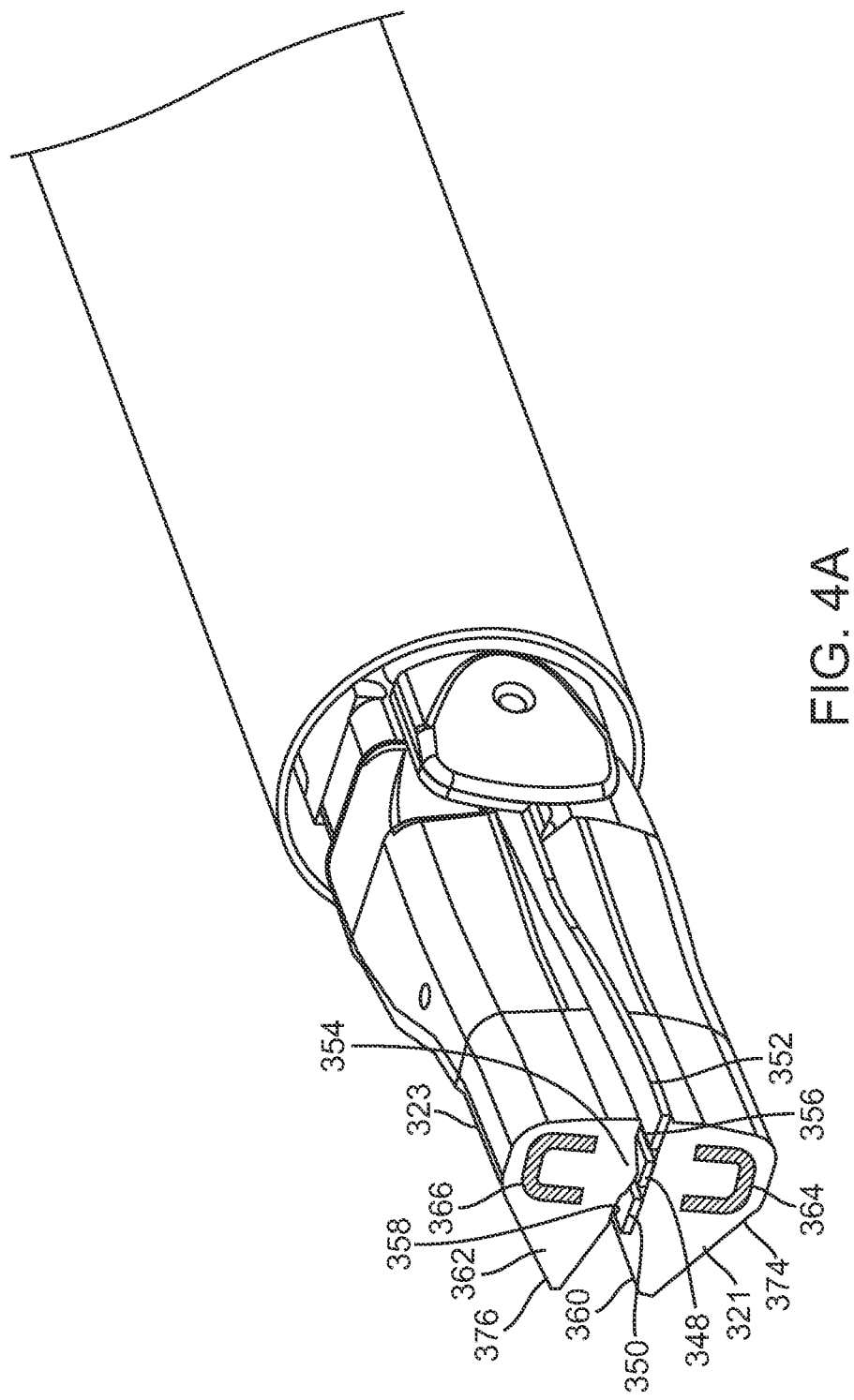

SURGICAL INSTRUMENT AND METHOD FOR USE

FIELD

This application relates to a surgical instrument, and more particularly, to a surgical instrument for use in a vessel harvesting procedure.

BACKGROUND

A significant area of cardiovascular disease involves the build up of plaque inside arteries that feed blood to the muscles of the heart. These deposits can cause occlusions which reduce or interrupt blood flow through these arteries. Coronary artery bypass grafting is a surgical procedure that has been used to address occlusions by creating an alternative blood path that bypasses the occluded artery.

Before a bypass surgery is performed, a vessel needs to be harvested from a patient's body for use as a conduit in the bypass surgery. In endoscopic vessel harvesting (EVH) surgical procedures, a long slender cannula with a working lumen may be inserted inside a patient, and advanced into a tunnel next to the saphenous vein in the patient's leg, the radial artery in the patient's arm, or any other targeted vessel for grafting. A surgical tool housed at least partially within the working lumen of the cannula may be placed along the saphenous vein to dissect the vessel away from adjacent tissue, and to sever side-branch vessels along the course of the vessel to be harvested. The surgical tool may be configured to grasp a vessel, and may include one or more operative elements for cutting and/or sealing the vessel. While the surgical tool is used to operate on tissue, an endoscope may be used to view the procedure.

Applicant of the subject application discovers that sometimes during the EVH procedure, blood, fatty tissue, debris, or other bodily substance may stick onto the lens of the endoscope, and/or may smear the endoscope lens. Thus, applicant of the subject application determines that it may be desirable to have a cleaning system for cleaning the lens of the endoscope during the EVH procedure, or during any procedure which requires the use of an endoscope or other types of imaging device.

SUMMARY

In accordance with some embodiments, an apparatus includes a tubular structure having a proximal end, a distal end, and a body extending between the proximal and distal ends, wherein the body includes a lumen for housing at least a part of an imaging device, and a fluid delivery channel that is fixed in position relative to the body, and an opening that is in fluid communication with the fluid delivery channel, wherein the fluid delivery channel has a first portion, and a second portion that forms an angle with an axis of the first portion.

In accordance with other embodiments, an apparatus includes a tube having a proximal end, a distal end, and a body extending between the proximal and distal ends, a lumen located in the body, wherein the lumen has a first portion that is parallel to a longitudinal axis of the body, and a second portion that forms an angle with the first portion, and an opening at a surface of the body, wherein the opening is in fluid communication with the second portion of the lumen.

In accordance with other embodiments, an apparatus includes a shaft having a proximal end, a distal end, and a body extending between the proximal and distal ends, a lumen in the body, a retractor attached to a rod, wherein at least a part of the rod is located within the lumen, and the retractor is slidable relative to the shaft, wherein the retractor comprises a first portion and a second portion, the first portion having a first tip, the second portion having a second tip, and wherein the first and second tips are separated from each other to define a space therebetween for allowing a vessel to enter therethrough, and wherein the first and second portions define a region having a first cross-sectional dimension that is larger than a second cross-sectional dimension perpendicular to the first cross-sectional dimension.

Other and further aspects and features will be evident from reading the following detailed description of the embodiments, which are intended to illustrate, not limit, the invention.

BRIEF DESCRIPTION OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments and are not therefore to be considered limiting of its scope.

FIG. 4A is a perspective cross sectional view of the pair of jaws of FIG. 3 in accordance with some embodiments;

DETAILED DESCRIPTION

Figure 1:
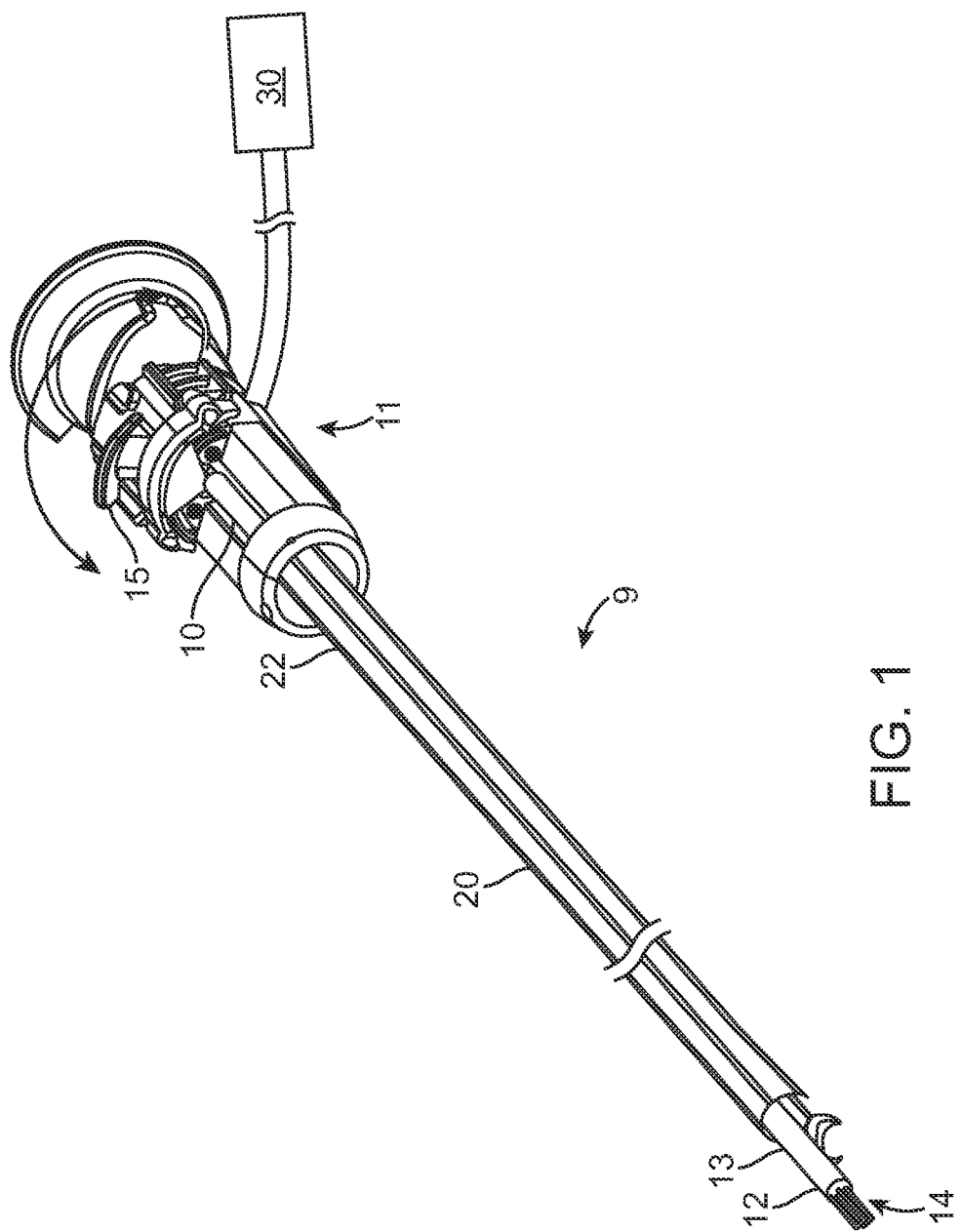
FIG. 1 illustrates a surgical instrument having a handle in accordance with some embodiments.

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

FIG. 1 illustrates a surgical instrument 9 in accordance with some embodiments. The surgical instrument 9 includes a handle 11, an elongated body 13 having a proximal end 10 and a distal end 12, and a surgical device 14 located at the distal end 12 of the body 13. As used in this specification, the term "surgical device" refers to any device or component that may be used to operate on tissue (e.g., to treat, manipulate, handle, hold, cut, heat, or energize, etc., tissue). The surgical instrument 9 also includes an elongated tube 20 having a lumen for housing at least a part of the elongated body 13. In some embodiments, the lumen may also house at least a portion of the surgical device 14. As used in this specification, the term "tube" or similar terms (e.g., "tubular structure") may refer to any device that has a tubular configuration, wherein the device may have a unity configuration (e.g., formed as a single structure), or may be an assembly formed from assembling different components together. Also, as used in this specification, the term "lumen" or similar terms (e.g., "bore," "opening," etc.) may refer to any space that is defined by any components. For example, a lumen of a tube may refer to any space that is defined at least partially by the tube, by a component of the tube, or a component/device that is located within the tube.

The elongated tube 20 has a proximal end 22 that is coupled to the handle 11. The proximal end 10 of the elongated body 13 is coupled to the handle 11 such that the body 13 (and therefore the surgical device 14) is rotatable and translatable relative to the tube 20. The elongated body 13 may be rigid, or alternatively, flexible. The handle 11 includes a manual actuator 15 that is coupled to the surgical device 14 (a tool) through linkage (not shown) within a bore of the body 13 for manually controlling an operation of the surgical device 14. The handle 11 and the actuator 15 may be made from insulative material(s) such as plastic. The details of the handle 11 will be described below.

The surgical instrument 9 is configured to be coupled to an energy source 30 during use. The energy source 30 is configured to deliver radiofrequency energy in some embodiments. In other embodiments, the energy source 30 is direct current (DC) source configured to deliver DC energy.

Figure 2A:
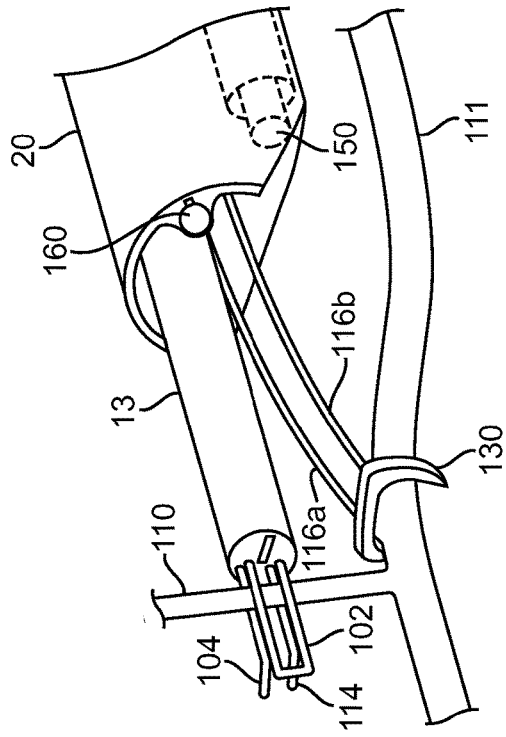
FIGS. 2A-2D illustrate a tool for cauterizing and cutting tissue in accordance with some embodiments.

FIG. 2A illustrates the surgical device 14 at the distal end of the surgical instrument 9 in accordance with some embodiments. The surgical device 14 includes a first electrode 102, a second electrode 104, and a cutter 106. The electrodes 102, 104 are fixedly coupled to the distal end of the body 13, and the cutter 106 is slidably mounted to the body 13. The cutter 106 is configured to slide in and out of a slot at the distal tip of the body 13. The first electrode 102 has a loop configuration that is formed by a wire. Similarly, the second electrode 104 also has a loop configuration that is formed by another wire. In other embodiments, the electrodes 102, 104 may have other configurations (e.g., shape, size, and form). The first and second electrodes 102, 104 function together as a pair of bi-polar electrodes during use. As shown in the figure, the electrodes 102, 104 are spaced apart from each other, thereby defining a space 108 therebetween for accommodating and securing a vessel (e.g., a side-branch vessel). As shown in the figure, the elongated tube 20 may optionally includes an endoscopic lumen 24 for housing an endoscope 150 during use. The surgical device 14 may be translated and/or rotated relative to the tube 20 (and hence, relative to the endoscope) by operating the actuator 15 at the handle 11. In some embodiments, the surgical instrument 9 may further include the endoscope 150.

Figure 2C:
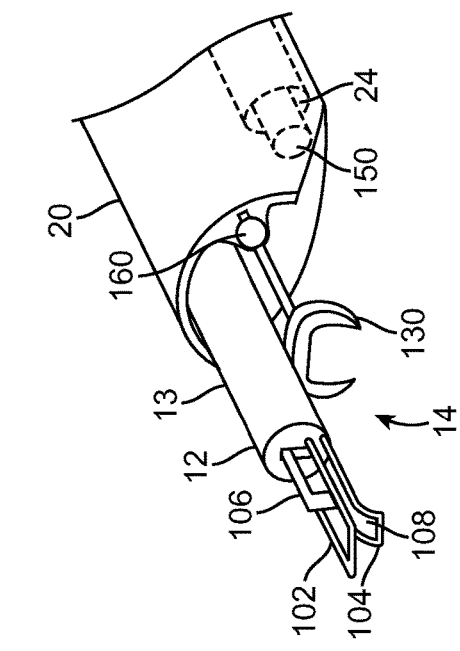
Figure 2B:
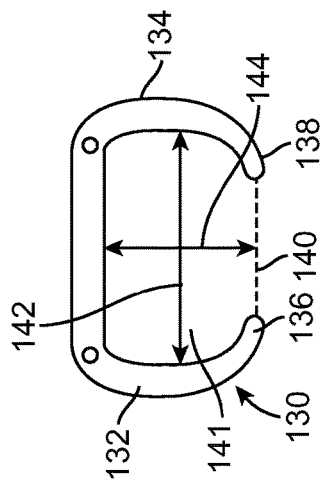

The distal end of the tube 20 may optionally further include a retractor 130 that is slidable relative to the elongated tube 20 and the body 13. The retractor 130 is attached to two rods 116a, 116b (FIG. 2B). As shown in the figure, the rods 116 have a curvilinear configuration such that when they are deployed out of the lumen of the tube 20, they curve away from the surgical tool/device 14. In other embodiments, the rods 116 may have a rectilinear or other configuration. As shown in the figure, the tube 20 has a cleaning device 160 for cleaning the lens of the endoscope 150 during use. Alternatively, one of the two rods 116 may have a fluid delivery lumen for delivering fluid (e.g., saline, water) towards the endoscope 150 for cleaning the lens of the endoscope during use.

Figure 2D:
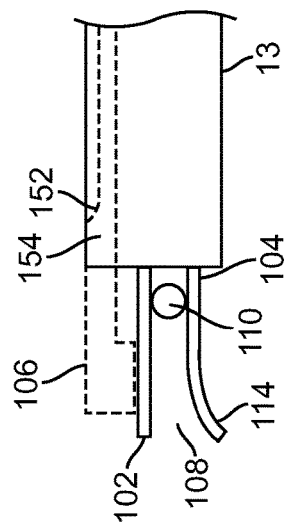
Figure 2E:
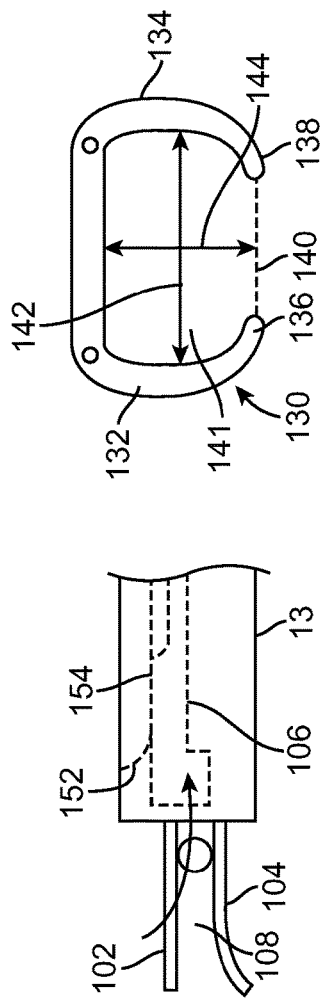
FIG. 2E illustrates a retractor for engaging a vessel in accordance with some embodiments.

The handle 11 may further include another actuator that is mechanically coupled by linkage (e.g., which may be the rods 116 themselves, or may be another component, e.g., a shaft, that couples to the two rods 116) housed within the tube 20 for moving the retractor 130 relative to the tube 20. The retractor 130 is configured to engage a main vessel 111 during use (FIG. 2B). As used in this specification, the term "retractor" may refer to any device or component that is configured to engage a vessel. Thus, the term "retractor" should not be limited to any particular device or component that retracts or moves in a certain way. In some embodiments, the retractor 130 may be considered to be a part of the surgical device/tool 14 at the distal end of the surgical instrument 9. As shown in FIG. 2E, the retractor 130 includes a first portion 132 with a first tip 136, and a second portion 134 with a second tip 138. The tips 136, 138 define a space 140 therebetween for allowing a vessel to enter therethrough. The first and second portions 132, 134 define a space 141 for accommodating the vessel once the vessel enters through the opening 140. In the illustrated embodiments, the space 141 has a dimension 142 that is longer to another dimension 144 perpendicular to the dimension 142. The space 141 has an elliptical shape. In other embodiments, the space 141 may have other shapes, such as a circular shape.

As shown in FIG. 2B, the electrodes 102, 104 may be configured (e.g., size, shaped, spaced apart by a certain distance, etc.) to capture a vessel 110 (e.g., a side branch vessel), while the retractor 130 engages with the main branch vessel 111. The cutter 106 is omitted in FIG. 2B for clarity purpose. The electrode 104 has a ramp portion 114 that allows the vessel 110 to be easily captured at the space 108. When the vessel 110 is captured between the electrodes 102, 104, energy may be delivered from an energy source 30 to the electrodes 102, 104, which function as bi-polar electrodes to deliver RF energy, thereby heating the vessel. The vessel may be heated to a temperature that welds/seals the vessel. When the vessel 110 is sealed, the actuator 15 at the handle 11 may be operated to slidably move the cutter 106 relative to the electrodes 102, 104 from a first position (FIG. 2C) to a second position (in the direction shown) to thereby cut the sealed vessel 110 (FIG. 2D). Such may be accomplished by providing a mechanical linkage housed within the body 13, which couples the actuator 15 to the cutter 106. As shown in the figures, the body 13 may include a protrusion at the interior wall that functions as a deflector 152 for causing the cutter 106 to move downward when a top portion 154 of the cutter 106 engages with the deflector 152.

Figure 3:
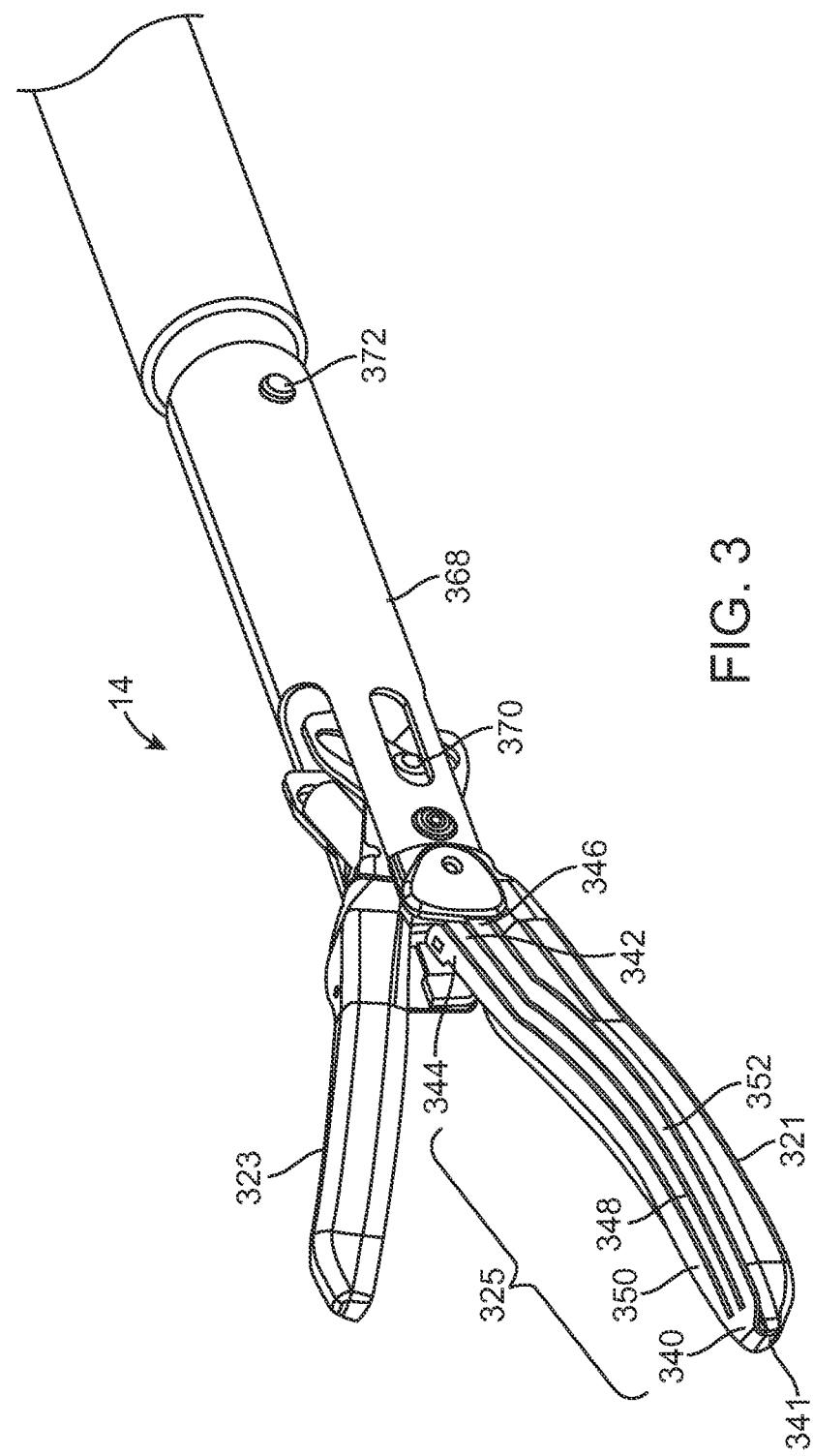
FIG. 3 is a perspective view of another tool for welding and cutting tissue in accordance with other embodiments, showing the tool having a pair of jaws.

It should be noted that the tool at the distal end of the surgical instrument 9 is not limited to the example shown in FIG. 2, and that the surgical instrument 9 may include other tools having different configurations in other embodiments. FIG. 3 illustrates another surgical device 14 at the distal end of the surgical instrument 9 in accordance with other embodiments. In the illustrated embodiments, the surgical device 14 is a jaw assembly that includes a pair of jaws 321, 323 for clamping, cutting, and sealing a vessel. The jaw 321 includes an electrically conductive material 325 which faces towards the opposing jaw 323. Alternatively, or additionally, the jaw 323 may include an electrically conductive material which faces towards jaw 321. The electrically conductive material 325 is in a form of an electrode, and is configured to provide heat during use. As used in this specification, the term "electrode" refers to a component that is for delivering energy, such as heat energy, RF energy, etc., and thus, should not be limited to a component that delivers any particular form of energy. The electrically conductive material 325 may be Ni-chrome, stainless steel, or other metals or alloys in different embodiments. The jaws 321, 323 are configured to close in response to actuation (e.g., pressing, pulling, or pushing, etc.) of the actuator 15, thereby clamping a vessel during use. In the illustrated embodiments, the actuator 15 may be further actuated (e.g., further pressed, further pulled, or further pushed, etc.) to cause the electrically conductive material 325 to provide heat, thereby cutting and sealing the clamped vessel. In particular, when the actuator 15 is further actuated, the electrically conductive material 325 is electrically coupled to an energy source 30 (e.g., a DC source), which provides a current to the electrically conductive material (electrode) 325, thereby heating the electrode 325. After the vessel is cut and sealed, the actuator 15 may be de-actuated to open the jaws 321, 323, thereby stopping the delivery of heat. The mechanical linkage for translating operation of the actuator 15 into closing and opening of the jaws 321, 323 may be implemented using cables, shafts, gears, or any of other mechanical devices that are known in the art. In other embodiments, a separate actuator (either on the handle 11 or otherwise coupled to the source 30, such as a separate foot pedal, etc.), may be provided for directing energy from the energy source 30 to the electrode 325. In such cases, the actuator 15 is for closing and opening the jaw assembly, and is not used to cause the energy source 30 to deliver energy to the electrode 325.

The linkage that mechanically couples the jaws 321, 323 to the actuator 15 may be electrically insulated, for example, by silicone rubber, ceramic or other suitable non-electrically conductive material. In some embodiments, energy is supplied from the energy source 30 via electric line housed by the body 13 to the electrically conductive material (electrode) 325 at jaw 321 (and/or electrode at jaw 323). In other embodiments, the body 13 may not include an electric line for delivering energy to the electrode 325. Instead, the linkage that mechanically couples the jaws 321, 323 to the actuator 15 may be electrically conductive, and is used to deliver energy to the electrode 325 at jaw 321 (and/or electrode at jaw 323).

As shown in the figure, the electrically conductive material 325 forms a heating element (electrode) 340 that is disposed on a surface of the jaw 321. The heater element 340 includes two outer portions 350, 352, and an inner (middle) portion 348. The outer portions 350, 352 have respective outer terminals 344, 346 at their ends, and the middle portion 348 has an inner terminal 342 at its end. Thus, the portions 348, 350, 352 form an electrical heater circuit between the center terminal 342 and outer terminals 344, 346. In the illustrated embodiments, the outer portions 350, 352 and the inner portion 348 function as an electrode that is configured to deliver heat during operation. In particular, during operation, the terminal 342 of the electrode 340 is electrically coupled to a first terminal of the DC source 30, and terminals 344, 346 of the electrode 340 are electrically coupled to a second terminal of the DC source 30, thereby allowing the electrode 340 to receive DC energy (e.g., for cutting and/or welding tissue). The heating element 340 may be formed using a single, flat sheet of electrically conductive material (e.g., Ni-chrome alloy, such as stainless steel at an outer layer, and Ni-chrome at an inner layer). This has reliability, manufacturing and cost advantages. It also reduces the likelihood of tissue build up and entrapment during use by not creating crevices into which the tissue can migrate.

As shown in FIG. 3, the jaw-operating mechanism and linkage thereof may be supported in a metal housing 368 that includes metal sliding pin 370 and attachment pin 372, all covered with an insulating layer of flexible material such as silicone rubber, or the like, to restrict energy discharges and to isolate tissue from moving parts. Also, such insulating cover retains the sliding and attachment pins 370, 372 in place to obviate the need for more expensive fasteners and mechanisms.

During use, current from the DC source 30 is conducted through the center terminal 342, and flows in the middle portion 348 of the heater element 340 and in parallel through the dual outer portions 350, 352 of the heating element 340 to the common terminals 344, 346. Thus, for heater portions 348, 350, 352 of equal thicknesses and equal widths, current density in the middle portion 348 is twice as high as the current density in each of the outer portions 350, 352 in response to electrical heater signal applied between terminal 342 and the common terminals 344, 346. Of course, current densities in the center and outer portions 348, 350, 352 may be altered (for example, by altering the relative widths of the heater portions, by altering resistances through selection of different materials, by altering both the widths and resistances, etc.) to alter the operating temperatures thereof in response to applied electrical heater signals. In operation, the outer heater portions 350, 352 may operate at a temperature sufficient to weld a tissue structure (e.g., a blood vessel) grasped between the jaws 321, 323, and the center heater portion 348 may operate at a higher temperature sufficient to sever the grasped tissue structure intermediate the welded segments.

Figure 4B:
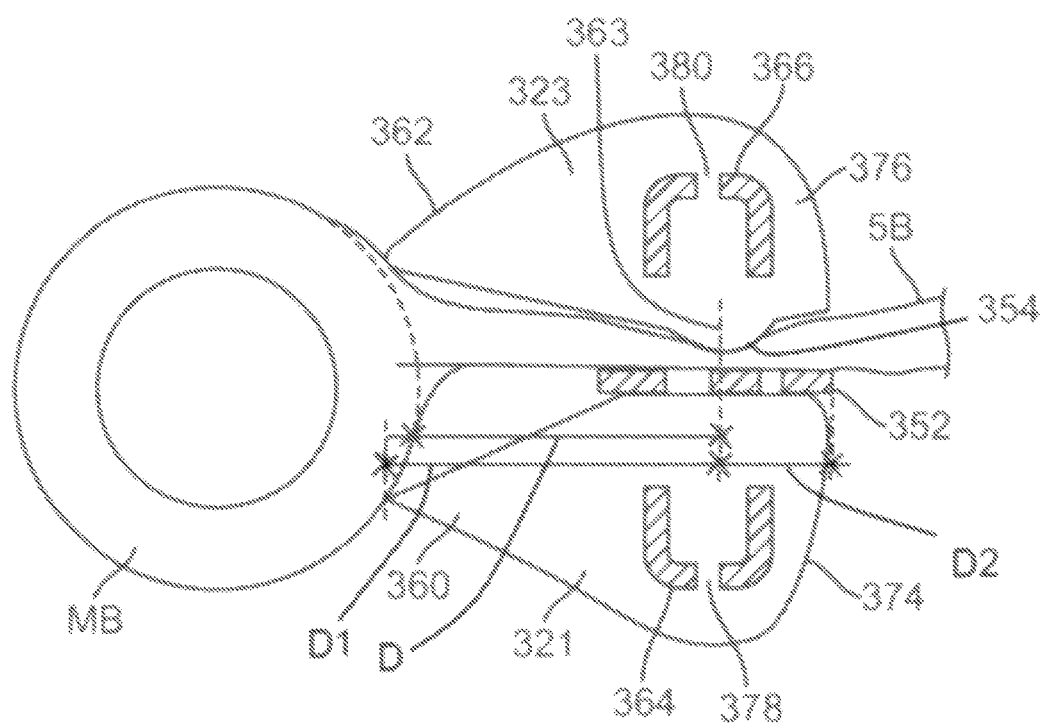
FIG. 4B is a cross sectional view of the pair of jaws of FIG. 4A, showing the jaws being used to cut a side branch vessel.

Referring now to FIG. 4A, there is shown a partial cross sectional perspective view of the jaws 321, 323 that illustrates the placement of heater portions 348, 350, 352. The jaw 321 includes a structural support 364, and the jaw 323 includes a structural support 366. The supports 364, 366 may be made from any materials, such as ceramic, polymers, stainless steel, or other metals or alloys. In some embodiments, the structural supports 364, 366 may be made from electrically conductive material that allows the supports 364, 366 to function as electrical lines (e.g., for transmitting current, RF signal, etc.). The structural supports 364, 366 are covered by respective layers 374, 376 of electrically insulating material, such as rubber, polymers, silicone, polycarbonate, ceramic or other suitable insulating material. The structural supports 364, 366 may include opening(s) 378, 380 along the length of the respective supports 364, 366 (FIG. 4B). This allows the layers 374, 376 to be overmolded onto the respective supports 364, 366 without using any adhesive to secure the layers 374, 376 relative to the respective supports 364, 366. In particular, as the layers 374, 376 are molded over the respective supports 364, 366, the molding material will flow through the openings 378, 380, thereby mechanically anchoring the layers 374, 376 relative to the respective supports 364, 366. As shown in the figure, the jaw 323 includes a surface elevation (protrusion) 354 substantially in alignment with the middle portion 348 in order to increase the compression force applied to a tissue structure grasped by the jaws 321, 323 and in contact with the middle portion 348. This promotes more efficient tissue severance, while adjacent regions 356, 358 of lower surface elevations on jaw 323 in alignment with the outer portions 350, 352 of the heater element introduce less compression force suitable for welding grasped tissue.

In the illustrated embodiments, the cross sections of the respective jaws 321, 323 are not symmetrical. Instead, jaw 321 has a protrusion 360, and jaw 323 has a protrusion 362. Each of the protrusions 360, 362 has a length so that when the protrusions 360, 362 abut against a main branch vessel MB, a cutting point 363 of the side branch vessel SB is at a prescribed distance D that is spaced away from the main branch vessel MB (FIG. 4B). In the illustrated embodiments, the distance D is at least 1 mm, and more preferably, at least 1.5 mm. In other embodiments, the distance D may have other values, such as that which is sufficient to prevent or minimize thermal spread from electrode 340 to the main branch vessel MB being harvested. The asymmetry caused by the protrusions 360, 362 results in a distance D1 between the cutting point 363 and the side of the jaws 321, 323 having the protrusions 360, 362 being greater than a distance D2 between the cutting point 363 and the side of the jaws 321, 323 opposite from the protrusions 360, 362. As illustrated in the embodiments, the protrusions 360, 362 are advantageous in that they help reduce thermal spread resulting from the cutting and sealing of the side branch vessel SB, thereby preserving the integrity of the main branch vessel MB that is being harvested. Also, the protrusions 360, 362 obviate the need for an operator to guess whether the cutting of the side branch vessel SB is sufficiently far (e.g., beyond a minimum prescribed spacing) from the main branch vessel MB. Instead, the operator merely abuts the protrusions 360, 362 of the jaw assembly against the main branch vessel MB, and the protrusions 360, 362 will automatically place the jaw assembly relative to the side branch vessel SB so that the side branch vessel SB is cut at a minimum prescribed distance D from the main branch vessel MB. In some cases, if the surgical instrument 9 is used to cut other types of tissue, such as nerves, organs, tendons, etc., the protrusions 360, 362 also provide the same benefits of preserving the integrity of tissue that is being cut, and obviating the need for a user to guess what is the appropriate margin. As shown in the figure, the protrusions 360, 362 diverge away from part of the side branch vessel SB. Such configuration allows part of the side branch vessel SB that is immediately next to the main branch vessel MB not to be clamped by the jaws. As a result, the end of the side branch vessel SB will fall away once it is cut. In other embodiments, the surgical instrument 9 does not need to include both protrusions 360, 362. Instead, the surgical instrument 9 may include either protrusion 360 or protrusion 362. Such configuration allows the device at the distal end of the instrument 9 to have a smaller profile, thereby allowing a user to effectively maneuver the distal device in tight tissue conditions.

As shown in the figure, the heater portion 352 may protrude laterally along, an outer edge of the closed jaws 321, 323. Such configuration may allow the heater portion 352 to deliver energy from the side of the jaw assembly even when the jaw assembly is closed. This may allow the heater portion 352 to heat tissue from a side of the jaw assembly during an operation, such as, for bleeding control. In other embodiments, the jaws may not include the protrusions 360, 362.

As shown in FIG. 3, the jaw assembly has a concave side and a convex side. In one method of use, while the jaw assembly is used to cut a side branch vessel SB, the jaw assembly is oriented so that its concave side faces towards the main branch vessel MB. The endoscope or viewing device may be placed next to the jaw assembly with the endoscope or viewing device viewing the concave side of the jaw assembly. This allows the user to better visualize the tip of the jaw assembly. Such configuration also provides a safety feature by allowing the user to know where the tips are during the vessel cutting procedure. Also as shown in FIG. 3, the exposed electrode portion 352 is on the convex side of the jaw assembly while the protrusions 360, 362 are on the concave side of the jaw assembly. The concavity provides extra spacing to protect the main branch vessel MB by keeping the distance along the side branch vessel SB even greater when it is grasped. Furthermore, having the exposed electrode 352 on the convex side creates an apex point that makes it easier to contact the side wall of the tunnel to address bleeding. In other embodiments, the protrusions 360, 362 may be on the convex side of the jaw assembly. In such cases, during use, the convex side of the jaw assembly would be oriented towards the main branch vessel MB, thereby ensuring that the tips of the jaw assembly are away from the main branch vessel MB to enhance protection (e.g., preventing the tip of the jaw assembly from touching or injuring the main branch vessel MB).

Figure 5:
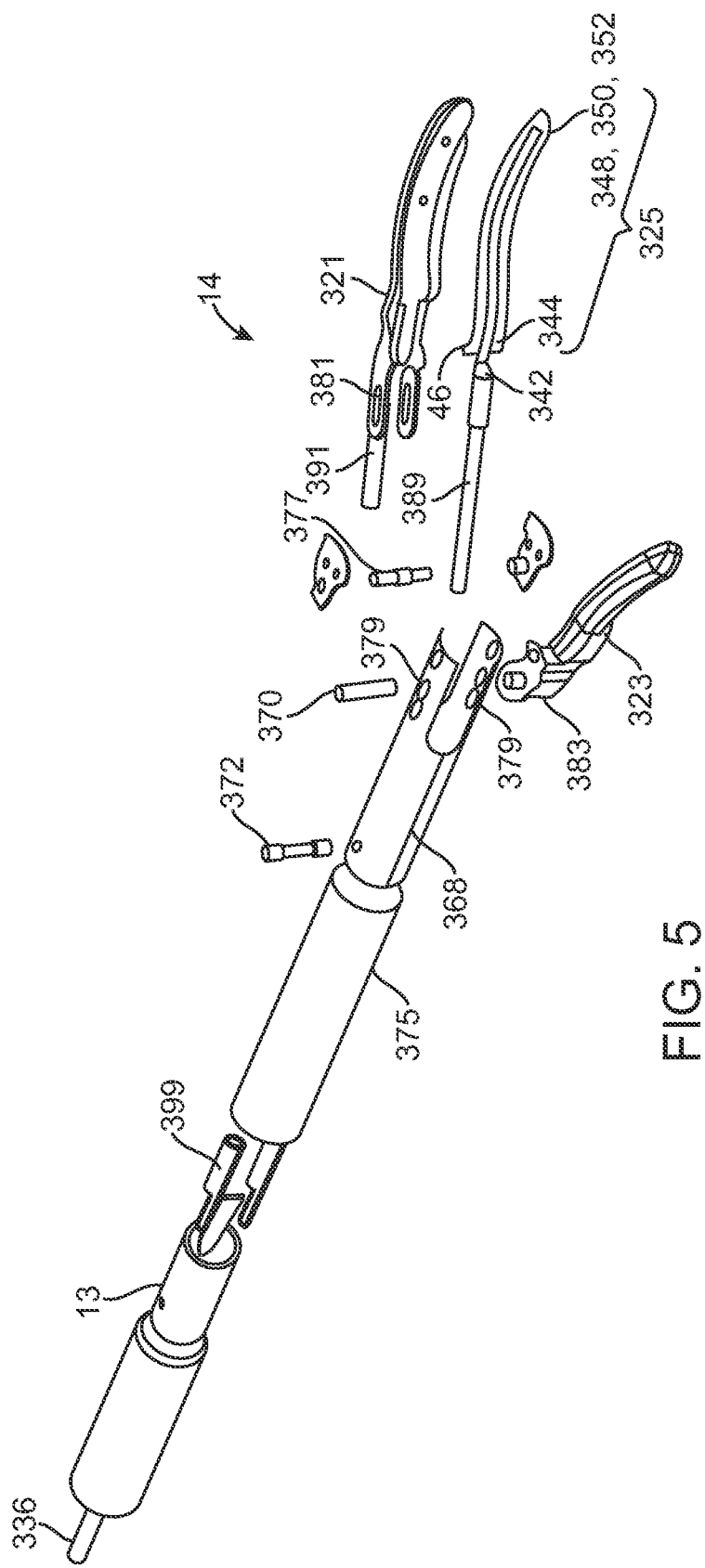
FIG. 5 is a partial exploded view of some components of a surgical instrument in accordance with some embodiments.

Referring now to FIG. 5, there is illustrated an exploded view showing some components of the surgical instrument 9. Specifically, the heater elements 348, 350, 352 (conductive material 325) are attached to jaw 321. Both jaws 321, 323 are pivotally attached via pin 377 to the metal housing 368. Pin 370 is disposed to slide within the aligned slots 379, and within the mating angled slots 381, 383 in the frame-mounts of the associated jaws to effect scissor-like jaw movement between open and closed positions as the slide pin 370 is moved relative to the pivot pin 377. Actuator rod 336 is linked to the slide pin 370, for example, via yoke 399. In the illustrated embodiments, the proximal end of the rod 336 is mechanically coupled to the actuator 15 at the handle 11. Axial movement of the rod 336 in one direction will cause the slide pin 370 to move towards the pin 377, thereby opening the jaws 321, 323. Axial movement of the rod 336 in the opposite direction will cause the slide pin 370 to move away from the pin 377, thereby closing the jaws 321, 323. An electrical conductor 389 connects to the inner terminal 342 of the heating element 348, 350, 352, and the outer terminals 344, 346 are electrically connected in common to conductor 391. In some embodiments, either conductor 389 or 391 may be housed within the wall or the bore of the elongated body 13. In other embodiments, if the rod 336 is electrically conductive, either conductor 389 or 391 may be coupled to the rod 336. In such cases, the rod 336 will be electrically coupled to one terminal of the DC source 30 during use. During use, the conductors 389, 391 may be electrically coupled to terminals of the DC source 30, which provides a current to thereby heat up the heater elements 348, 350, 352. The center heater element 348 is configured to cut a vessel (e.g., a side branch vessel) while the outer heater elements 350, 352 are configured to weld (seal) the vessel. In some embodiments, parts of the surgical device 14 may be insulated via an outer insulating layer for isolating certain components from biologic tissue and fluids.

In any of the embodiments described herein, the jaw assembly at the distal end of the surgical instrument 9 does not need to include all of the features described herein. For example, in some embodiments, the jaw assembly does not include outer electrode portions 350, 352. Instead, the jaw assembly includes one electrode strip (like the middle electrode portion 348 described above) for cutting or sealing tissue. Furthermore, in other embodiments, the jaw 323 may not have the raised portion 354. Instead, the jaw 323 may have a flat surface that is for contacting the electrode portions 348, 350, 352. In addition, in further embodiments, the jaws 321, 323 may not include the respective protrusions 360, 362. Instead, the cross section of the jaw 321/23 may have a symmetrical configuration. In other embodiments, protrusion(s) may be provided on both sides of the jaw assembly (e.g., one or more protrusions at the concave side of the jaw assembly, and one or more protrusions at the convex side of the jaw assembly). Such configuration provides buffering on both sides of the jaw assembly, and allows for correct placement of the jaw assembly regardless of which side (the concave or convex side) of the jaw assembly is oriented towards the main branch vessel MB during use. In further embodiments, instead of the curved configuration, the jaws could be straight. Also, in any of the embodiments described herein, instead of, or in addition to, using the jaw assembly for cutting and/or welding of vessel tissue, the jaw assembly may be used for transection of other types of tissue, such as fatty and connective tissue encountered during a vessel harvesting procedure or other procedures.

Figure 6A:
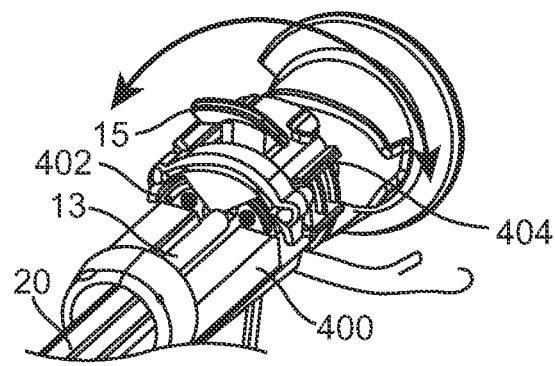
FIG. 6A illustrates components of the handle of FIG. 1 in accordance with some embodiments.

FIG. 6A illustrates the handle 11 of the surgical instrument 9 of FIG. 1 in accordance with some embodiments. The handle 11 includes a support portion 400, a carriage 402 slidably mounted to the support portion 400, the actuator 15, and a coupler 404 for coupling the actuator 15 to the carriage 402. As used in this specification, the term "support portion" may refer to any part of a handle, relative to which the carriage 402 or the actuator 15 may move, and does not need to provide any particular form of support for the remaining components of the handle. Thus, the term "support portion" should not be limited to a base or any other parts of the handle. During use, the actuator 15 may be moved by a finger (e.g., thumb, index finger, etc.) laterally as indicated by the arrow shown. Movement of the actuator 15 moves the coupler 404 relative to the carriage 402, thereby rotating the body 13 (and hence, the surgical device/tool 14) relative to the tube 20.

Figure 6B:
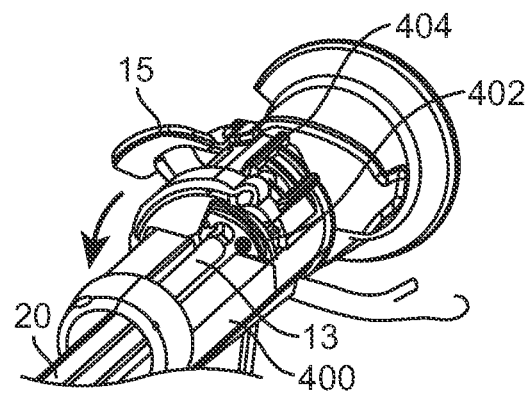
FIGS. 6B and 6C illustrate the handle of FIG. 1, showing a control being operated in different configurations.

For example, the actuator 15 may be moved laterally towards the right side (FIG. 6B), thereby rotating the coupler 404 about an axis that is parallel to the longitudinal axis of the handle 11. Rotation of the coupler 404 relative to the carriage 402 actuates a gear system at the carriage 402, thereby turning the body 13 (and hence, the surgical device/tool 14) relative to the tube 20 in the same direction as the rotation of the coupler 404. During use, either the actuator 15 or the coupler 404 may be operated by the user's finger to rotate the tube 20.

Figure 6C:
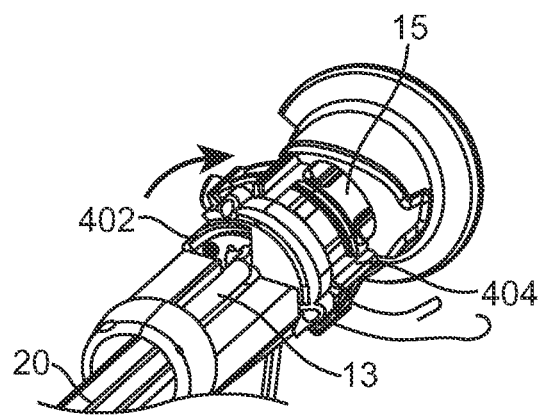

Similarly, the actuator 15 may be moved laterally towards the left side (FIG. 6C), thereby rotating the coupler 404 about an axis that is parallel to the longitudinal axis of the handle 11. Such rotation of the coupler 404 relative to the carriage 402 actuates a gear system at the carriage 402, thereby turning the body 13 (and hence, the surgical device/tool 14) relative to the tube 20 in the same direction as the rotation of the coupler 404. During use, either the actuator 15 or the coupler 404 may be operated by the user's finger to rotate the tube 20.

Figure 7:
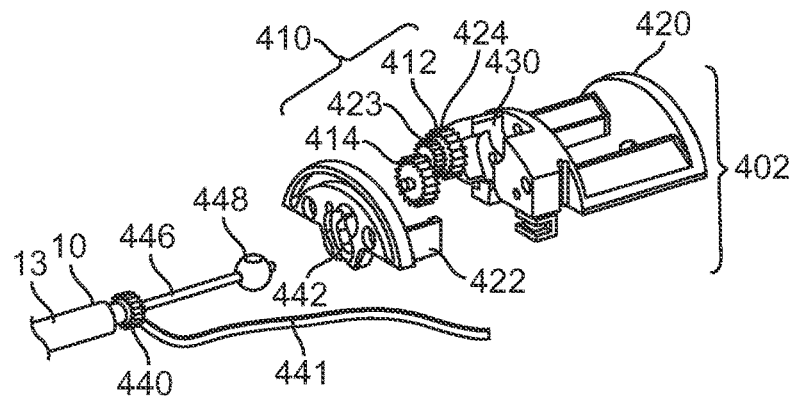
FIG. 7 illustrates some components of the handle of FIG. 1 in accordance with some embodiments.

FIGS. 7-11 illustrate some components of the handle 11. As shown in FIG. 7, the handle 11 includes a gear system 410 having a first gear 412 and a second gear 414 mounted between a first carriage portion 420 and a second carriage portion 422, wherein the first and second carriage portions 420, 422 together form the carriage 402. The first gear 412 includes a small gear 423 and a large gear 424, and is rotatably mounted to the carriage 402. The small gear 423 and the large gear 424 are fixedly secured to each other. The second gear 414 is also rotatably mounted to the carriage 402, and engages with the small gear 423. The carriage 402 includes an opening 430 for allowing a part of the large gear 424 to be accessed. As shown in the figure, a gear 440 is fixedly secured to the proximal end 10 of the body 13. The proximal end 10 with the gear 440 extends through an opening 442 at the carriage 402, thereby allowing the gear 440 to be engaged with the second gear 414. Also, as shown in the figure, wires that are connected to the electrodes 102, 104 (in the embodiments of FIG. 2) or to terminals at the electrode 325 (in the embodiments of FIG. 3) may be housed in a cable 441, which extends out of the body 13 and through a central opening at the gear 440. In some embodiments, the wires may be coupled to the energy source 30. In other embodiments, if the handle 11 is also used to deliver energy to the surgical device/tool 14, then at least one of the wires may be connected to a switch located in the handle 11.

Figure 8:
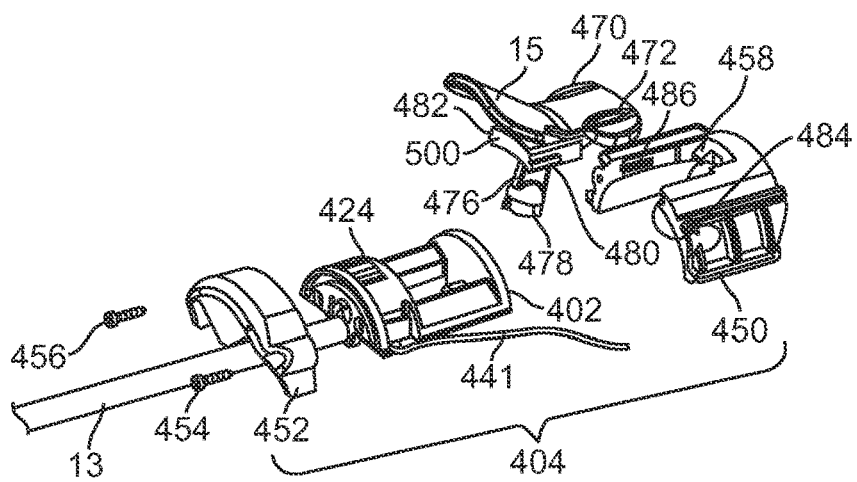
FIGS. 8 and 9 illustrate additional components of the handle of FIG. 1 in accordance with some embodiments.
Figure 9:
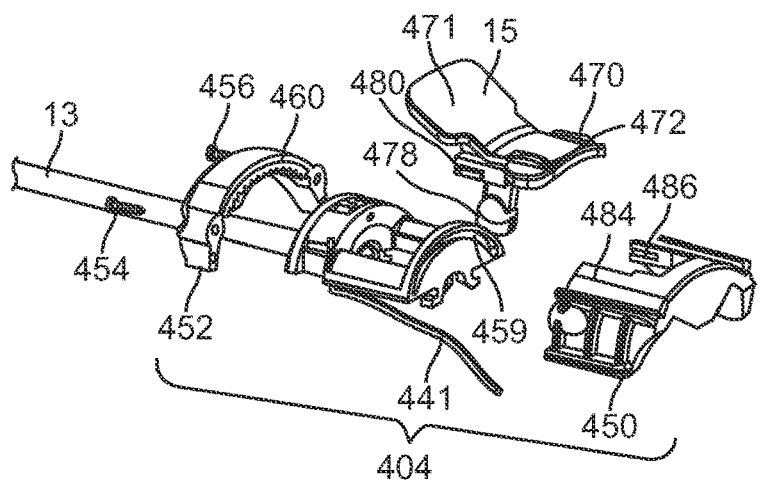

As shown in FIGS. 8 and 9, the coupler 404 includes a first coupler portion 450 and a second coupler portion 452, which are secured to each other via two screws 454, 456. The coupler 404 also includes a protrusion 458, which is configured (e.g., sized and shaped) to engage with a slot 459 at the carriage 402. The slot 459 guides the motion of the coupler 404 so that the coupler 404 will move relative to the carriage 402 in a defined path (e.g., in a curvilinear path). The coupler 404 also includes a ring gear 460, which is configured to engage with the large gear 424 at the opening 430 of the carriage 402. Although the actuator 15 and the coupler 404 have been described as separate components, in other embodiments, the coupler 404, or any of its components, may be considered to be a part of the actuator 15. Also, although the carriage 402 and the coupler 404 have been described as separate components, in other embodiments, the coupler 404, or any of its components, may be considered to be a part of the carriage 402.

Also, as shown in the figures, the actuator 15 includes a surface 471 for allowing manipulation of the actuator 15 by a finger, and protrusions 470, 472 for preventing the finger from sliding off the edge of the actuator 15 during use. During use, the actuator 15 may be moved laterally towards the right side (such as that shown in FIG. 6B) to push the coupler 404 to rotate relative to the carriage 402 in the direction of actuation. The rotation of the coupler 404 relative to the carriage 402 causes the ring gear 460 to move relative to the carriage 402, thereby turning the large gear 424 at the opening 130. Since the large gear 424 is fixedly secured to the small gear 423, rotation of the large gear 424 will rotate the small gear 423 in the same direction as that of the large gear 424. Rotation of the small gear 423 turns the second gear 414, which in turn, rotates the gear 440 at the proximal end 10 of the body 13. Thus, the second gear 414 is for causing the body 13 and the surgical device 14 to rotate in the same direction as that of the actuator 15. Also, during use, the actuator 15 may be moved laterally towards the left side (such as that shown in FIG. 6C) to push the coupler 404 to rotate relative to the carriage 402 in the direction of actuation. This will result in the body 13 rotating in the same direction as the direction of actuation, as similarly discussed.

In some embodiments, the gear system may be configured (e.g., by selecting a desired gear ratio, gear size, number of gears, etc.) such that a relatively small amount of movement by the actuator 15 will result in a rotation of the body 13 and the surgical device 14 through a large angular range. For example, in some embodiments, a rotation of the actuator 15 through an angular range of +/−40° or less will result in turning of the body 13 and the surgical device 14 by +/−180° or more of 40°. Thus, by moving the actuator 15 from the left-most position to the right-most position (or vice versa), the body 13 and the surgical device 14 may be turned 360°. Such configuration is beneficial in that it achieves amplification of motion for the body 13, thereby allowing the body 13 and the surgical device 14 to be rotated relative to the handle 11 efficiently. In should be understood that during use of the surgical instrument 9, the body 13 does not always need to be rotated 360°. For example, a user may want to rotate the body 13 and the surgical device 14 by an angle $\theta_t$ that is less than 360°. In such cases, the user may rotate the actuator 15 by an angle $\theta_c$ to a desired position as determined by the user, thereby rotating the body 13 and the surgical device 14 by a desired angular range $\theta_t$. As discussed, $\theta_t$ is larger than $\theta_c$. In some embodiments, the gear system may be configured such that a movement by the actuator 15 will result in a relatively smaller rotation of the body 13 and of the surgical device 14, for finer control of angular position. In such cases, $\theta_t$ is less than $\theta_c$. In some embodiments, $\theta_t$ and $\theta_c$ may be governed by the relationship: $\theta_t = k\, \theta_c$, wherein k represents an amplification factor when k>1, and represents a reduction factor when k<1. In some cases, k is a constant that is based on the design of the gear system.

Figure 10:
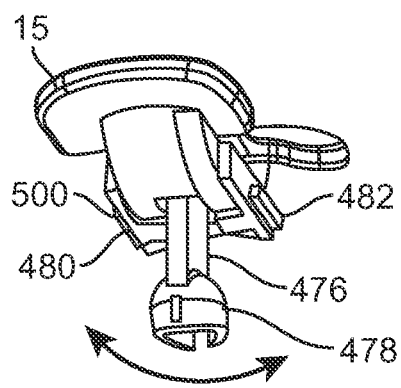
FIG. 10 illustrates an actuator of the handle of FIG. 1 in accordance with some embodiments.
Figure 11:
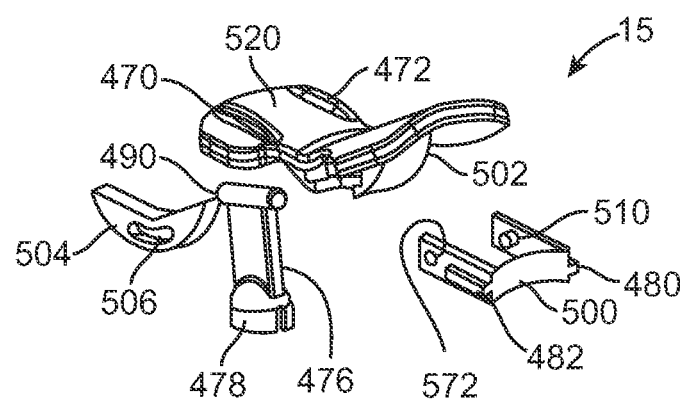
FIG. 11 illustrates some components of the actuator of FIG. 10 in accordance with some embodiments.

In the illustrated embodiments, the actuator 15 is slidably coupled to a base 500 (FIG. 10). The base 500 has projections 480, 482 on either side of the base 500 for engagement with respective slots 484, 486 at the coupler 404 (see FIGS. 9-11). The actuator 15 is also rotatably coupled to an arm 476 via the shaft 490. In particular, the shaft 490 is housed within a slot formed by a first actuator portion 502 and a second actuator portion 504 (FIG. 11). The shaft 490 allows the arm 476 to be pivotable relative to the actuator 15 in the direction shown in FIG. 10. Such tilting motion allows the actuator 15 to be moved laterally (as in FIG. 6B or 6C) along an arc-path with a center that is offset from a longitudinal axis of the body 13. In other embodiments, if the arc-path of the actuator's 15 movement has a center that coincides with a longitudinal axis of the body 13, then the tilting of the arm 476 relative to the actuator 15 is not required. The actuator portion 504 has a slot 506 for slidable engagement with a protrusion 512 at the base 500. Similarly, the actuator portion 502 has a slot (with the same configuration as that of slot 506) for slidable engagement with a protrusion 510 at the base 500. The arm 476 has a socket 478 at its end for mating with a sphere 448 at an end of a rod 446 that extends out of the body 13. In some embodiments, the rod 446 may be coupled to the cutter 106 in the embodiment of FIG. 2 for actuating movement of the cutter 106. In other embodiments, the rod 446 may be the shaft 336 in the embodiment of FIG. 5 for actuating movement of the jaw assembly. The socket 478 together with the sphere 448 forms a ball joint that allows the arm 476 to move in different degrees of freedom with respect to the rod 446. In any of the embodiments described herein the arm 476 and/or the base 500 may be considered to be a part of the actuator 15. In other embodiments, the arm 476 and/or the base 500 may be considered to be a part of the coupler 404.

When the surface 471 of the actuator 15 is pressed down towards the base 500, the slidable engagement between the slot 506 and the protrusion 512 at the base 500 will guide the actuator 15 to move in a curvilinear path (defined by the shape of the slot 506). In the illustrated embodiments, the pressing of the surface 471 of the actuator 15 will cause the actuator 15 to move proximally relative to the base 500. This in turn causes the bottom end of the arm 476 to move proximally to pull the ball joint, thereby pulling the rod 446 backward. This in turn pulls the cutter 106 at the distal end of the surgical instrument 9 proximally. Alternatively, in the case of the embodiment of FIG. 5, this will in turn pull the rod 336 proximally to close the jaw assembly. After the surface 471 is pressed down, the rear surface 520 of the actuator 15 will be moved to a higher elevation. The user may press the rear surface 520 downward against the base 500 so that the actuator 15 is slidably moved distally relative to the base 500, as governed by the slidable engagement between the slot 506 and the protrusion 512. This in turn causes the bottom end of the arm 476 to move distally to push the ball joint, thereby pushing the rod 446 distally. This in turn pushes the cutter 106 at the distal end of the surgical instrument 9 distally. Alternatively, in the case of the embodiment of FIG. 5, this will in turn push the rod 336 distally to open the jaw assembly.

Also, during use, the actuator 15 (or the coupler 404) may be pushed distally so that the carriage 402 together with the body 13 and the surgical device 14 is translated distally relative to the tube 20. Alternatively, the actuator 15 (or the coupler 404) may be pulled proximally so that the carriage 402 together with the body 13 and the surgical device 14 is translated proximally relative to the tube 20.

In some embodiments, the handle 11 may further includes an electrical contact, such that when the actuator 15 is further pulled proximally, the electrical contact will close a conductive path, thereby allowing a current to be delivered from the energy source 30 to the electrodes 102, 104, or to the electrode 325 at the jaw assembly. For example, the cable 441 may carry a first wire connected to a first terminal at the electrode 325, and a second wire connected to a second terminal at the electrode 325. At the proximal end, the first wire may be electrically connected to the electrical contact at the actuator 15, and a receiving contact (not shown) in the handle 11 may be coupled to a first terminal at the energy source 30. Also, at the proximal end, the second wire may be coupled to a second terminal at the energy source 30. During use, the actuator 15 may be pulled all the way to the back to engage the electrical contact at the actuator 15 with the receiving contact, thereby closing a conductive path formed by the energy source 30, the electrode 325, and the first and second wires, and allowing energy to be delivered from the energy source 30 to the electrode 325. In other embodiments, the actuator 15 is not configured to cause delivery of energy from the energy source 30 to the electrodes 102, 104, or to the electrode 325.

As illustrated in the above embodiments, the handle 11 is advantageous in that it allows rotation and/or translation of the body 13 (and hence, the surgical device 14) relative to the tube 20, and movement of a component of the surgical device 14, to be accomplished by manipulation of a single actuator 15. In some embodiments, the control may be configured to be operated like a joystick so that it can be used to rotate the tool 14 (e.g. by moving the control left or right) and translate the tool 14 (e.g., by moving the control forward or backward), wherein the translation of the tool 14 may be done simultaneously or separately from the rotation of the tool 14. Such joystick like control may also allow actuation of a component (e.g., a cutting element, a jaw, an electrode, etc.) of the tool 14 (e.g. by providing a pivitable or depressable control surface, such as a button). In some cases, the actuator 15 also allows delivery of energy from the energy source 30 to the surgical device 14. The handle 11 is also advantageous in that it rotates the surgical device 14 by a large angular amount in response to a relatively small movement of the actuator 15, thereby providing amplification of movement of the surgical device 14.

During use of the surgical instrument 9 to harvest a vessel, the tube 20 is inserted into the patient's body through an opening (e.g., an incision through the patient's skin). The endoscope 150 may be placed inside the tube 20 for viewing at distal end while a surgical procedure is being performed by the surgical device 14. In some cases, the endoscope 150 may optionally include a light source and/or fiber optics for illuminating the target site. The distal end of the tube 20 is placed next to a vessel that is desired to be harvested, such that the longitudinal axis of the tube is approximately parallel to the vessel. The retractor 130 is then deployed to engage and capture the vessel. The tube 20 is then advanced distal along the length of the vessel. When a side branch vessel is encountered, the user may then operate the handle 11 to deploy the surgical device 14 for cutting and/or sealing the side branch vessel. In particular, various components (e.g., the actuator 15 and/or the coupler 404) of the handle 11 may be operated to translate the surgical device 14 proximally or distally relative to the tube 20 (as described herein), and/or to rotate the surgical device 14 relative to the tube 20 (as described herein), thereby placing the surgical device 14 at an operative position relative to the side branch vessel for operation on the side branch vessel.

The handle 14 may then be further used to cause the surgical device 14 to cut and/or seal the side branch vessel. For example, for the embodiments of FIG. 2, the actuator 15, or another actuator on the handle 11, or a control at the energy source 30, may be operated to cause energy to be delivered to the electrodes 102, 104, thereby heating the side branch vessel, and sealing it. The actuator 15 may then be operated (or further operated) to pull the cutter 106 proximally to cut the sealed vessel, as described herein. For the embodiments of FIG. 3, the actuator 15 may be operated to close the jaws 321, 323 to grasp and compress the side branch vessel. Power is then supplied using the DC source 30 to the heater elements 48, 50, 52 (which function as resistive element that heats up in response to the delivered direct current) to effect tissue welds at tissues that are in contact with outer segments 50, 52, and to effect tissue cutting at tissue that is in contact with segment 48.

Figure 12:
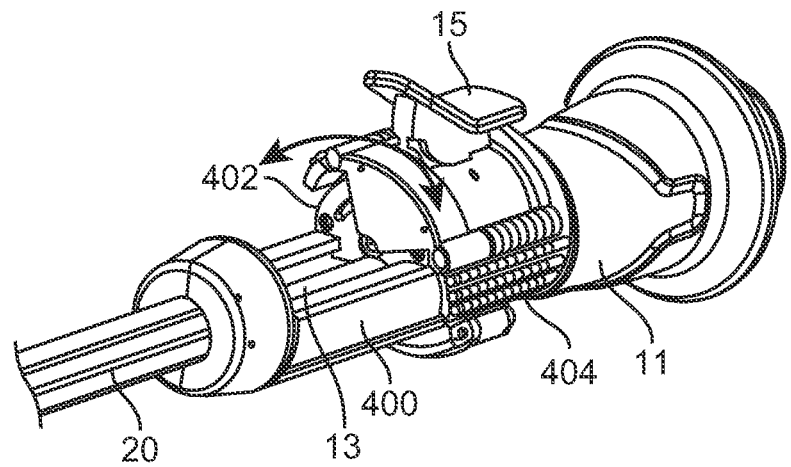
FIG. 12 illustrates a surgical instrument having another handle in accordance with other embodiments.

FIG. 12 illustrates another handle 11 in accordance with other embodiments. In the illustrated embodiments, the handle 11 is similar to the embodiments described previously, except that the coupler 404 is configured to move laterally to control a rotation of the surgical device/tool 14 independent of the actuator 15. In such cases, the actuator 15 and/or the coupler 404 is for translating the surgical device/tool 14 longitudinally relatively to the tube 20. The actuator 15 may also be used for moving a component (such as the cutter 106, the jaw members, etc.) of the surgical device/tool 14, as similarly discussed. However, unlike the embodiments of FIGS. 6-11, the actuator 15 cannot be used to rotate the surgical device 14 relative to the tube 20. Instead, rotation of the surgical device 14 relative to the tube 20 is performed by moving the coupler 404 in either direction shown in the figure. The handle 11 of FIG. 12 has components that are the same as those in the previous embodiments, except that the actuator 15 is not configured to move laterally with the coupler 404. Thus, in the illustrated embodiments, the actuator 15 may be coupled to a base (e.g., base 500) that is fixedly secured to the carriage 402.

Figure 13:
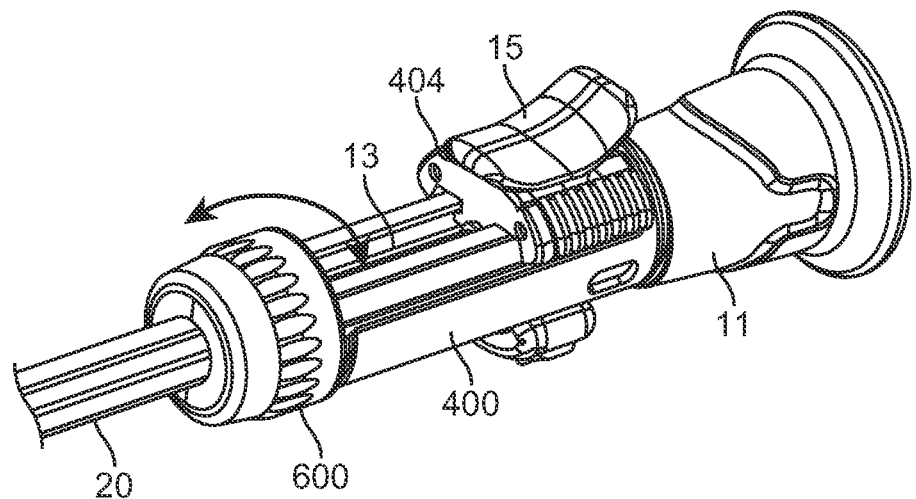
FIG. 13 illustrates a surgical instrument having another handle in accordance with other embodiments.

FIG. 13 illustrates another handle 11 in accordance with other embodiments. The handle 11 includes a ring 600 located distal to the actuator 15 for rotating the body 13 (and hence the surgical device/tool 14). The ring 600 is circumferentially disposed at the handle 11 so that it may be conveniently manipulated by one or more fingers of a user. In the illustrated embodiments, the operation of the ring 600 is independent from the operation of the actuator 15. Thus, the actuator 15 and/or the coupler 404 may be used to translate the body 13 distally or proximally relative to the tube 20 without involving the ring 600. The actuator 15 may also be used to move a component (e.g., the cutter 106, the jaws, etc.) of the surgical device/tool 14 without involving the ring 600. Also, the ring 600 may be used to rotate the body 13 without involving the actuator 15 and the coupler 404.

Figure 14:
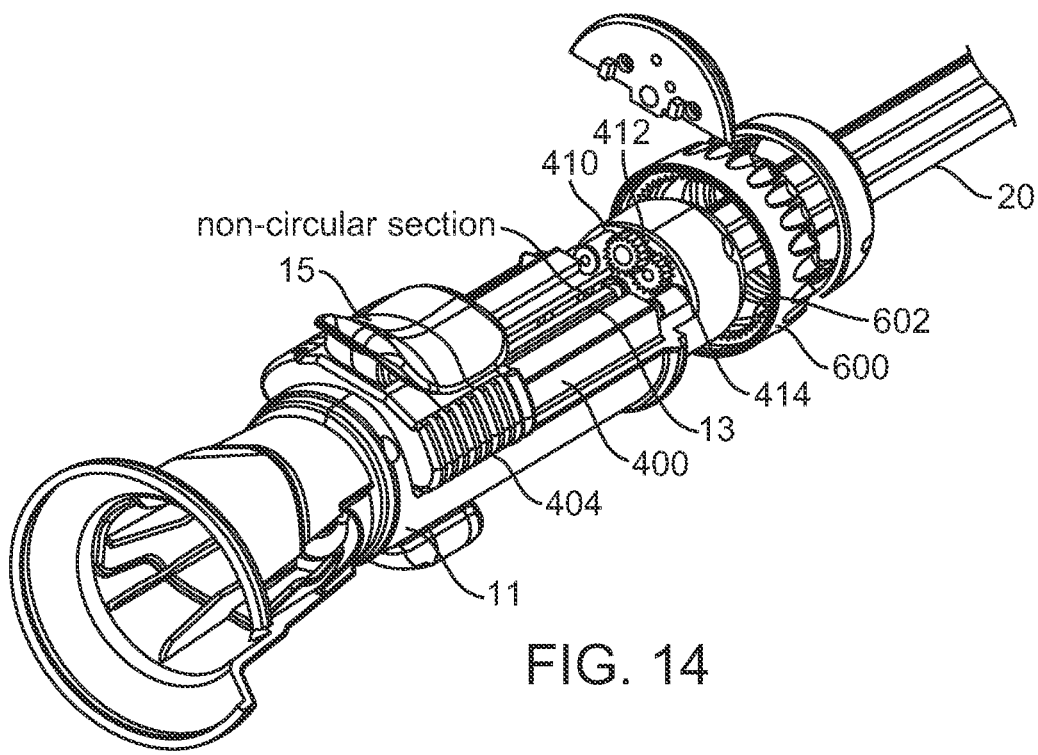
FIG. 14 illustrates some components of the handle of FIG. 13.

FIG. 14 illustrates some components of the handle 11 of FIG. 13 in accordance with some embodiments. In the illustrated embodiments, the handle 11 includes many components that are the same as those of FIGS. 6-11. However, unlike the previous embodiments, the handle 11 does not include the carriage 402, and the coupler 404 is not rotatably coupled to the carriage 402. Instead, the coupler 404 is slidably coupled to the support 400. This allows the body 13 and the surgical device 14 to be translated relative to the body 20 by translational movement of the coupler 404 (or the actuator 15) relative to the support 400. The handle 11 also includes the gear system 410 having the gears 412, 414. However, unlike the previous embodiments of FIG. 6, the gear system 410 is not coupled to the moveable carriage 402. Instead, the gear system 410 is coupled to a portion of the handle 11 that is fixed relative to the support 400. As shown in the figure, the ring 600 has a ring gear 602 located circumferentially at an interior surface of the ring 600. The ring gear 602 is configured to engage with the gear 412 during use. The body 13 has a non-circular cross section (such as a square section) so that it can transmit rotation from the gear train to the tool, as well as allow sliding of the tool back and forth. In other embodiments, the body 13 can have other cross sectional shapes.

In some embodiments, the gear system 410 may be configured (e.g., by selecting a desired gear ratio, gear size, number of gears, etc.) such that a relatively small amount of movement by the ring 600 will result in a rotation of the body 13 through a large angular range. For example, in some embodiments, a rotation of the ring 600 through an angular range of +/−40° or less will result in turning of the body 13 by +/−180° or more. Thus, by turning the ring 600 over a small angular range, the body 13 may be turned 360°. Such configuration is beneficial in that it achieves amplification of motion for the body 13, thereby allowing the body 13 to be rotated relative to the handle 11 efficiently. In should be understood that during use of the surgical instrument 9, the body 13 does not always need to be rotated 360°. For example, a user may want to rotate the body 13 by an angle $\theta_t$ that is less than 360°. In such cases, the user may rotate the ring 600 by an angle $\theta_c$ to a desired position as determined by the user, thereby rotating the body 13 by a desired angular range $\theta_t$. As discussed, $\theta_t$ is larger than $\theta_c$. In some embodiments, the gear system may be configured such that a movement by the actuator 15 will result in a relatively smaller rotation of the body 13 and of the surgical device 14, for finer control of angular position. In such cases, $\theta_t$ is less than $\theta_c$. In some embodiments, $\theta_t$ and $\theta_c$ may be governed by the relationship: $\theta_t = k\, \theta_c$, wherein k represents an amplification factor when k>1, and represents a reduction factor when k<1. In some cases, k may be a constant that is based on the design of the gear system.

Figure 15:
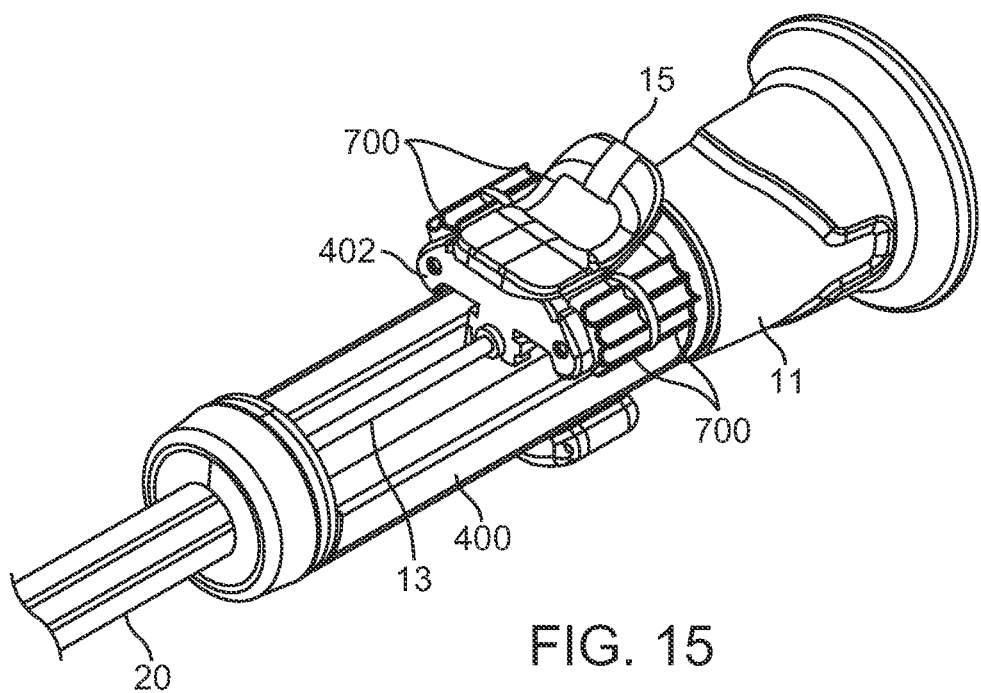
FIG. 15 illustrates a surgical instrument having another handle in accordance with other embodiments.

FIG. 15 illustrates another handle 11 in accordance with other embodiments. The handle 11 includes a plurality of wheels 700 located at a periphery of the handle 11. The wheels 700 are rotatably coupled to the carriage 702 through the gear system 410 that is housed inside the carriage 702. In the illustrated embodiments, the handle 11 is similar to the embodiments of FIG. 6, except that it doesn't have the coupler 404, and rotation of the body 13 is not controlled by the actuator 15. In such cases, the actuator 15 and/or the wheels 700 may be pushed distally or pulled proximally for translating the surgical device/tool 14 longitudinally relatively to the tube 20. The actuator 15 may also be used for moving a component (such as the cutter 106, the jaw members, etc.) of the surgical device/tool 14, as similarly discussed. However, unlike the embodiments of FIGS. 6-11, the actuator 15 cannot be used to rotate the surgical device 14 relative to the tube 20. Instead, rotation of the surgical device 14 relative to the tube 20 is performed by turning any one of the wheels 700. The handle 11 of FIG. 15 has components that are the same as those in the previous embodiments, except that the handle does not include the coupler 404, and the actuator 15 is not configured to move laterally. Thus, in the illustrated embodiments, the actuator 15 may be coupled to a base (e.g., base 500) that is fixedly secured to the carriage 402.

In some embodiments, the gear system 410 may be configured (e.g., by selecting a desired gear ratio, gear size, number of gears, etc.) such that a relatively small amount of movement by any one of the wheels 700 will result in a rotation of the body 13 through a large angular range. For example, in some embodiments, a rotation of the wheel 700 through an angular range of +/−40° or less will result in turning of the body 13 by +/−180° or more. Thus, by turning the wheel 700 over a small angular range, the body 13 may be turned 360°. Such configuration is beneficial in that it achieves amplification of motion for the body 13, thereby allowing the body 13 to be rotated relative to the handle 11 efficiently. In should be understood that during use of the surgical instrument 9, the body 13 does not always need to be rotated 360°. For example, a user may want to rotate the body 13 by an angle $\theta_t$ that is less than 360°. In such cases, the user may rotate the wheel 700 by an angle $\theta_c$ to a desired position as determined by the user, thereby rotating the body 13 by a desired angular range $\theta_t$. As discussed, $\theta_t$ is larger than $\theta_c$. In some embodiments, the gear system may be configured such that a movement by the actuator 15 will result in a relatively smaller rotation of the body 13 and of the surgical device 14, for finer control of angular position. In such cases, $\theta_t$ is less than $\theta_c$. In some embodiments, $\theta_t$ and $\theta_c$ may be governed by the relationship: $\theta_t = k\, \theta_c$, wherein k represents an amplification factor when k>1, and represents a reduction factor when <1. In some cases, k is a constant that is based on the design of the gear system.

It should be noted that the handle 11 should not be limited to the examples described previously, and that the handle 11 may have different configurations in different embodiments. For example, in other embodiments, the handle 11 may not include all of the features described previously. Also, in other embodiments, the handle 11 may have other shapes and forms. Furthermore, in any of the embodiments described herein, in addition to the control (e.g., the actuator 15, the coupler 404, the ring 600, the wheel(s) 700, or any combination of the foregoing) described, the handle 11 may further include additional control(s) for performing other functions. As used in this specification, the term "control" may refer to any of the components of the handle 11, or any combination of the components of the handle 11.

Also, it should be noted that the surgical device/tool 14 of the surgical instrument 9 should not be limited to the examples described above, and that the surgical instrument 9 may include other tools 14 in other embodiments. For example, although the above embodiments have been described with reference to the surgical device 14 being for clamping, cutting, and/or sealing vessel (e.g., saphenous vein, an artery, or any other vessel), in other embodiments, the surgical device 14 may be any have different configurations, and different functionalities. For example, in other embodiments, the surgical device 14 may be clip appliers or grasping jaws for grasping other types of tissues.

The cleaning system 160 for cleaning the lens of the endoscope 150 will now be described with reference to FIGS. 16-21. For clarity purpose, the surgical device 14 and the retractor 130 are omitted in these figures.

Figure 16A:
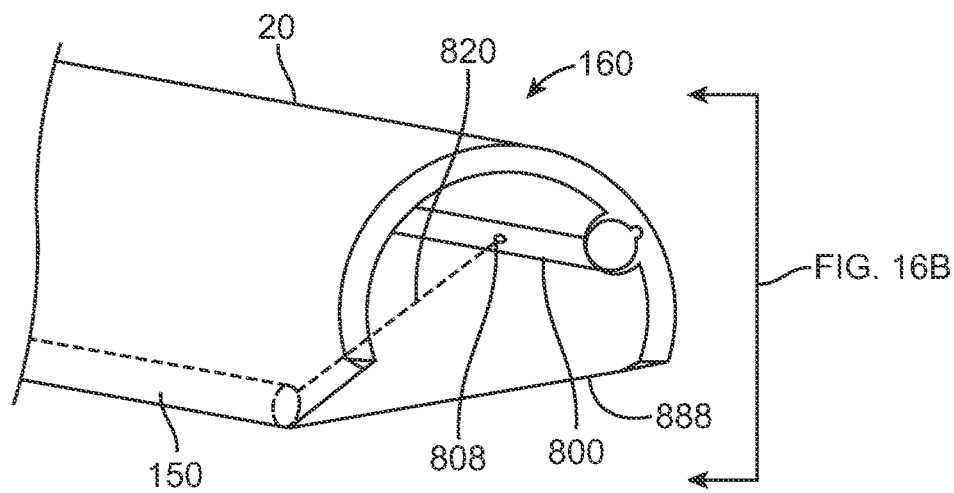
FIGS. 16A and 16B illustrate a distal end of a surgical instrument having a washing system in accordance with some embodiments.
Figure 16B:
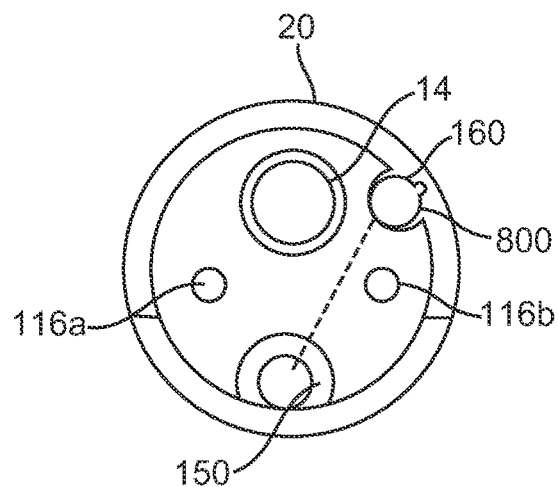
Figure 17:
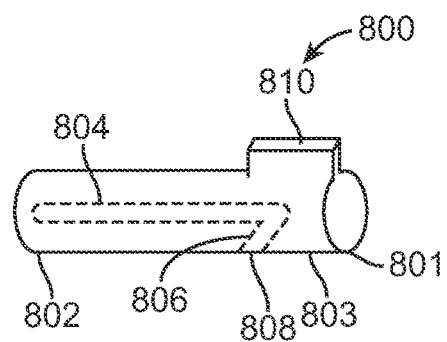
FIG. 17 illustrates a component of the washing system of FIG. 16 in accordance with some embodiments.

FIGS. 16A and 16B illustrate the cleaning system 160 that includes a tubular structure 800 in accordance with some embodiments. As shown in FIG. 17, the tubular structure 800 has a distal end 801, a proximal end 802, and a body 803 extending between the ends 801, 802. The tubular structure 800 also has a first channel 804 that extends along the length of the tubular structure 800, and a second channel 806 that forms an angle with the first channel 804. In the illustrated embodiments, the angle may be a value that is between 20° and 40°, such as 30°. In other embodiments, the angle may be other values, as long as the fluid can be delivered to the lens of the endoscope 150. The second channel 806 is in fluid communication with the first channel 804, and ends with an opening 808 that is located at an exterior surface of the tubular structure 800. The tubular structure 800 also includes a protrusion 810 that is configured to mate with a slot at the tube 20 (FIG. 16A). In other embodiments, the protrusion 810 is optional, and the tubular structure 800 may not include the protrusion 810. The tubular structure 800 may be secured to the tube 20 via an adhesive. In further embodiments, the structure 800 and the distal portion of the tube 20 may be integrally formed by a molding process to have a unity configuration.

As shown in FIG. 16B, the cleaning system 160 is located at a radial angle relative to the lens of the endoscope 150 such that the cleaning system 160 is not directly across from the endoscope 150. Such configuration allows the tool 14 to be directly across the endoscope 150 without having the cleaning system 160 interfering with the tool 14. Also, such configuration allows the opening 808 to be aimed at the lens of the endoscope 150 such that the fluid injection path does not intercept the tool 14 and the support structures 116a, 116b of the retractor 130. In other embodiments, the cleaning system 160 may be directly across from the endoscope 150. In such cases, the tool 14 may be located at a radial angle relative to the endoscope 150 such that it is not directly across from the endoscope 150. Thus, in other embodiments, the cleaning system 160 may be located at any position relative to the endoscope 150 (e.g., the cleaning system 160 may be implemented at any location along the circumferential cross section of the tube 20). Also, in other embodiments, the cleaning system 160 may be configured so that the opening 808 is pointed towards other directions (e.g., for providing cleaning function at other target sites).

Figure 18:
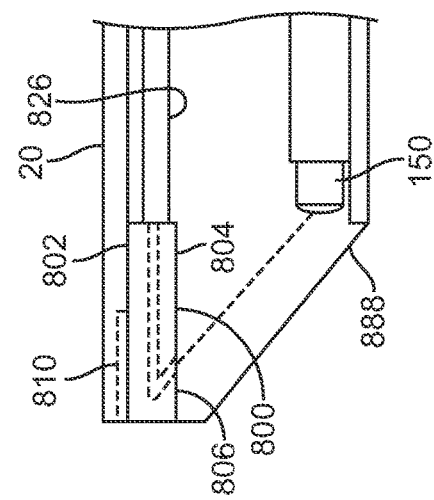
FIG. 18 illustrates a cross sectional side view of the washing system of FIG. 16.

FIG. 18 illustrates a partial side view of the distal end of the tube 20 in accordance with some embodiments. As shown in the figure, the proximal end 802 of the tubular structure 800 is coupled to a fluid delivery tube 826. During use, the proximal end of the fluid delivery tube 826 is connected to a fluid source, such as a syringe. If the user determines that the lens of the endoscope 150 needs to be cleaned, the user may operate on the syringe to cause fluid (e.g., saline, water, etc.) to be delivered from the syringe to the tubular structure 800 via the tube 826. The fluid is delivered through the channel 804 and the channel 806, and out of the opening 808. As shown in the figure, the second channel 806 is oriented such that fluid exiting from the opening 808 is directed proximally towards the lens of the endoscope 150, thereby cleaning the lens of the endoscope 150.

Figure 19:
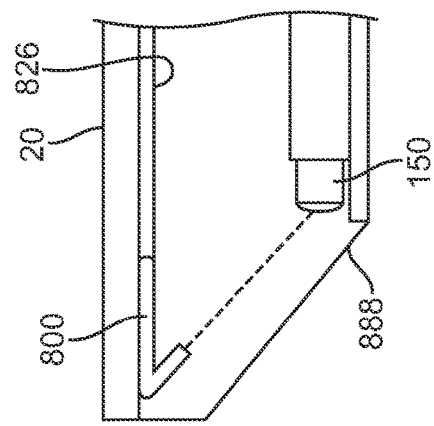
FIG. 19 illustrates another washing system in accordance with other embodiments.
Figure 20:
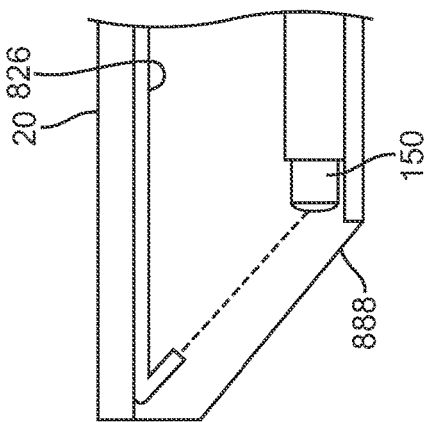
FIG. 20 illustrates another washing system in accordance with other embodiments.

It should be noted that the cleaning system 160 should not be limited to the example described previously, and that the cleaning system 160 may have other configurations in other embodiments. For example, in other embodiments, the cleaning system 160 may include a tubular structure 800 that is in a form of a bent tube (FIG. 19). In other embodiments, instead of having a tubular structure coupled to the fluid delivery tube 826, the cleaning system 160 may include just the fluid delivery tube 826 having a bent distal end (FIG. 20). The fluid delivery tube 826 may be secured to the tube 20 using an adhesive or a mechanical coupler. In any of the embodiments described herein, the tube 20 may include a distal section that is mechanically attached (e.g., via an adhesive or a mechanical coupler) to a remaining part of the tube 20. In such cases, the cleaning system 160 may be coupled to the distal section of the tube 20.

Figure 21:
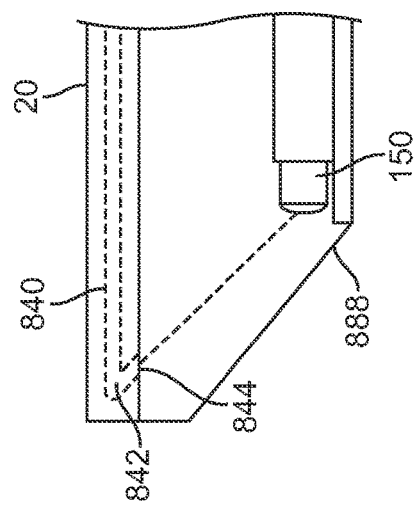
FIG. 21 illustrates another washing system in accordance with other embodiments.

In further embodiments, the cleaning system 160 may be implemented by providing fluid delivery channels 840, 842 within the wall of the tube 20 (FIG. 21). In such cases, the interior surface of the wall of the tube 20 will include an opening 844 for allowing fluid to be exiting therethrough. In some embodiments, the tube 20 may include a distal section that is mechanically attached (e.g., via an adhesive or a mechanical coupler) to a remaining part of the tube 20. In such cases, the cleaning system 160 may be implemented at the distal section of the tube 20.

Also, as shown in the above embodiments, the distal end of the tube 20 does not have any wall near the location where the endoscope 150 is located. In particular, the tube 20 has a cut-out section 888 at the distal end next to the endoscope 150, which allows fluid from the cleaning system 160 to escape without being trapped inside the tube 20 (wherein trapped fluid may obstruct the view of the endoscope). The tube 20 with the cut-out section may be formed by removing a section of a tube that is used to construct the tube 20. Alternatively, the tube 20 with the cut-out section may be formed by molding the tube 20 to have the configuration shown. In other embodiments, the distal end of the tube 20 does not have the cut-out section.

Figure 22:
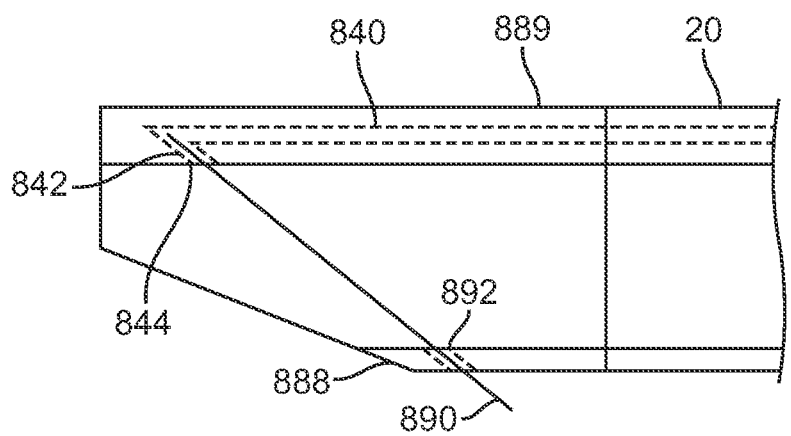
FIG. 22 illustrates a technique for forming a distal portion of a tube that includes a fluid delivery channel.

In some embodiments, the distal end of the tube 20 may be a separate component that is separately formed from a remaining part of the tube 20, and is then coupled to the remaining part of the tube 20. For example, the distal end of the tube 20 may be molded to have an unity configuration. In some cases, such distal end of the tube 20 may be molded to have the cut-out section 888, and the fluid delivery channels 840, 842 (such as those shown in FIG. 21). One technique for forming the channel 842 at the distal component 889 of the tube 20 is to place a pin 890 relative to the material of the distal component 889 like that shown in FIG. 22. The pin 890 may be longer and may have a bent configuration so that it can also be used to form the channel 840. Such technique may result in the distal component 889 having an opening 892 through the wall of the component 889. Such opening 892 may be used to drain fluid during use. For example, in some cases, cleaning fluid that is delivered from the opening 844 may escape through the cut-out section 888 and through the opening 892.

Also, in any of the embodiments described herein, instead of using the cleaning system 160 to clean the lens of the endoscope, the cleaning system 160 may be used to clean other devices, such as another imaging device, a window of a component that is used to house an endoscope or another type of imaging device, or other surgical tools.

Figure 23:
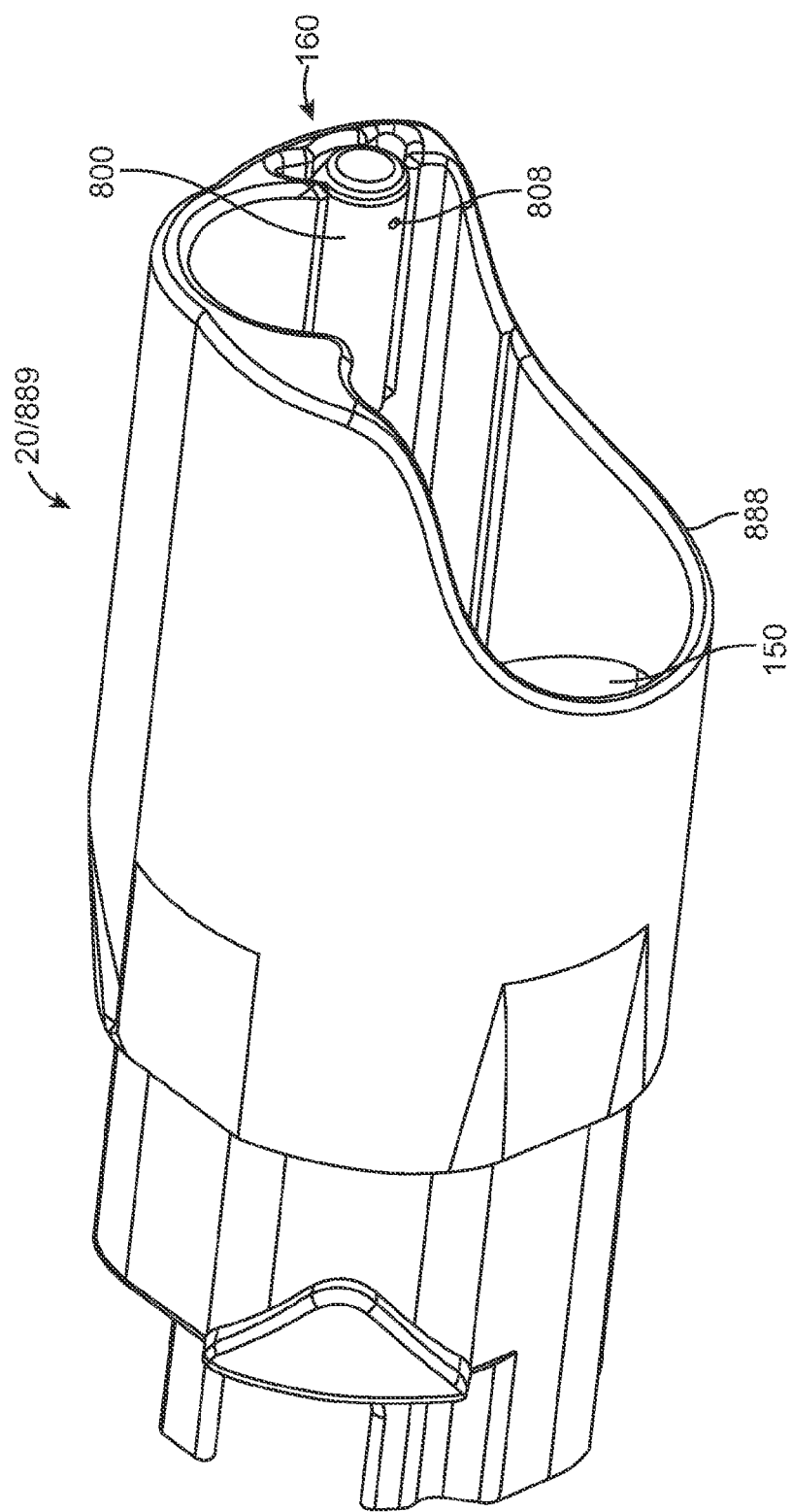
FIGS. 23 and 24 illustrate a distal end of a surgical instrument having a washing system in accordance with other embodiments.
Figure 24:
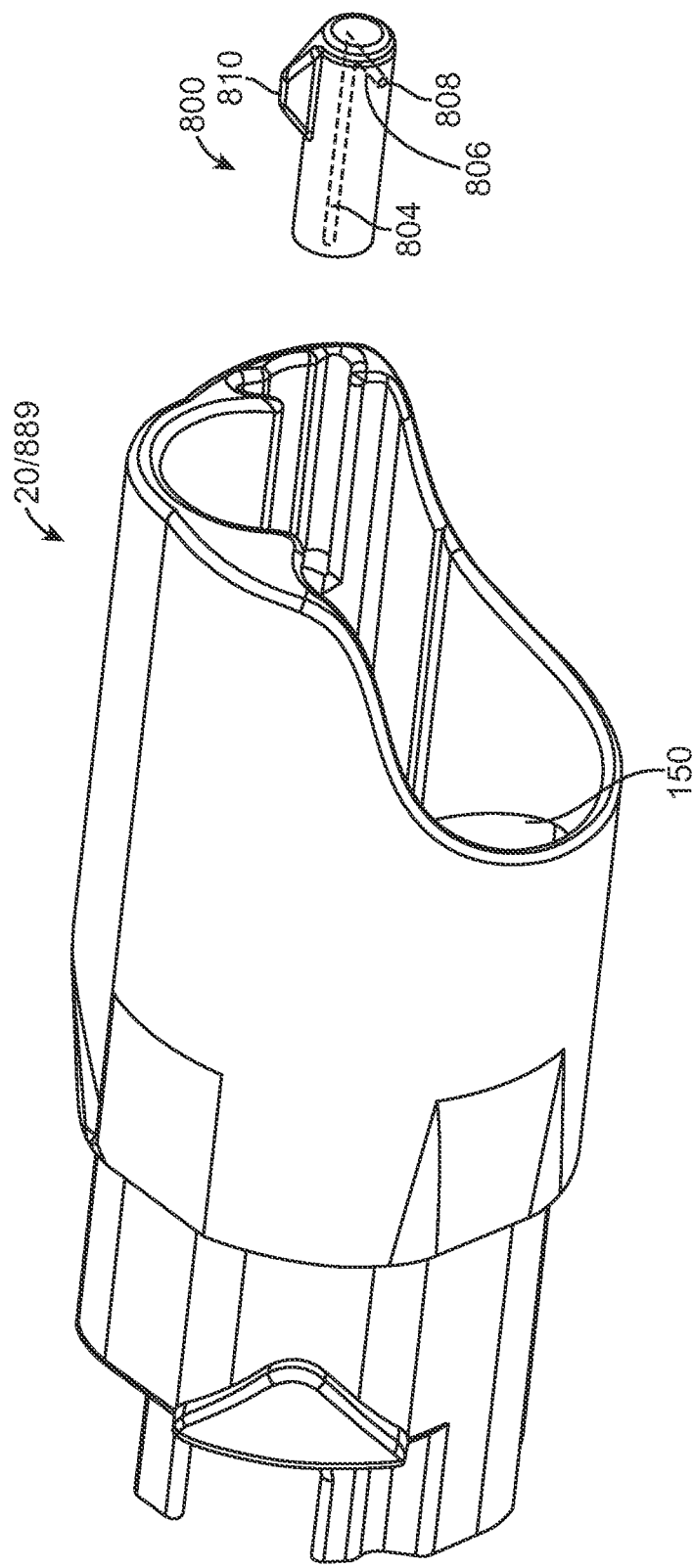
Figure 25:
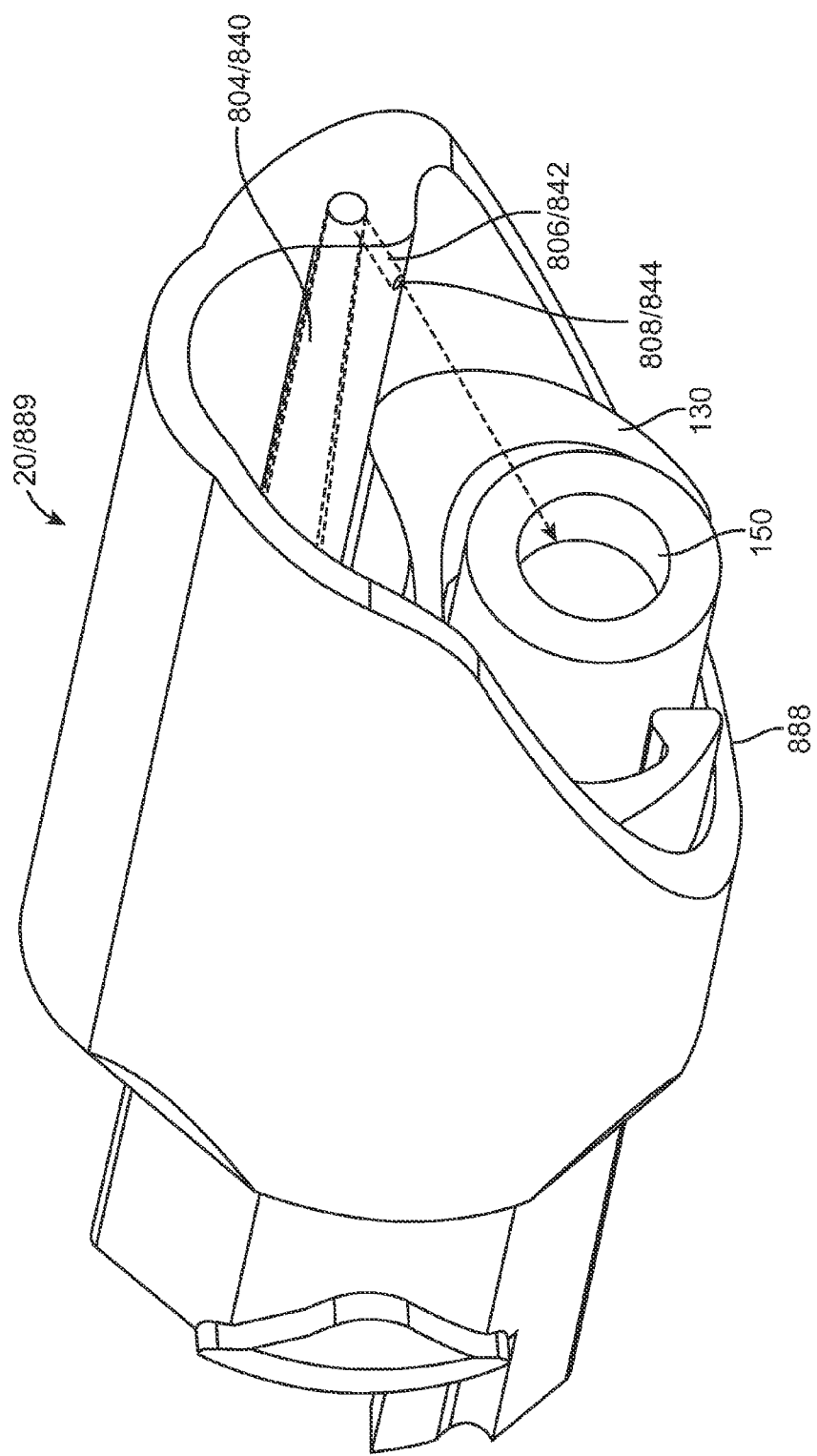
FIG. 25 illustrates a distal end of a surgical instrument having a washing system in accordance with other embodiments.

It should be noted that the distal end 20/889 of the surgical instrument is not limited to the configurations described previously, and that the distal end 20/889 of the surgical instrument may have other configurations in other embodiments. For example, in other embodiments, instead of the configuration shown in FIGS. 16-17, the distal end of the tube 20/component 889 may have the configuration shown in FIGS. 23 and 24. Also, in other embodiments, instead of the configuration shown in FIG. 21, the distal end of the tube 20/component 889 may have the configuration shown in FIG. 25.

Although particular embodiments have been shown and described, it will be understood that they are not intended to limit the present inventions, and it will be obvious to those skilled in the art that various changes and modifications may be made without departing from the spirit and scope of the present inventions. The specification and drawings are, accordingly, to be regarded in an illustrative rather than restrictive sense. The present inventions are intended to cover alternatives, modifications, and equivalents, which may be included within the spirit and scope of the present inventions as defined by the claims.

What is claimed:
1. A surgical system, comprising:
a tube having an axis, a proximal end, and a distal end;

a retractor slidable relative to the tube, wherein the retractor comprises:
a distal portion extendable relative to the distal end of the tube, the distal portion of the retractor comprising a first tip and a second tip spaced apart from one another to define a space therebetween for grasping a main vessel; and
a surgical device separate from the retractor, the surgical device having a first jaw and a second jaw for grasping through a clamping motion a branch vessel of the main vessel, wherein the first and second jaws are extendable relative to the distal end of the tube and are relatively movable with respect to one another by a pivot rotation about a hinge from a first open position, wherein the first and second jaws are spaced apart from one another, to a second closed position, wherein the first and second jaws are closer in proximity to one another than the first position,
wherein the first jaw comprises an electrode supported by a first jaw surface, the electrode comprising a first terminal and a second terminal, the electrode is configured to deliver heat upon the receipt of electrical DC energy from a DC energy source, wherein the first terminal is electrically coupled to a first terminal of the DC energy source and the second terminal is electrically coupled to a second terminal of the DC energy source;
wherein the first jaw comprises a lateral protrusion extending lengthwise along the first jaw, lateral sides of the first jaw having an asymmetrical cross-section due to the lateral protrusion extending from the jaw in a direction substantially parallel to a reference line that is substantially perpendicular to the axis of the tube and extending, the cross-section taken substantially perpendicular to the axis of the tube;
wherein the lateral protrusion is configured for abutting the main vessel and positioning the main vessel apart from a portion of the branch vessel clamped between the first and second jaws in the second position; and
wherein the lateral protrusion of the first jaw is spaced apart from the second jaw when the first and second jaws are brought into a position of closest proximity with respect to one another.

2. The system of claim 1, wherein the distal portion of the retractor has a C-shape configuration and wherein the surgical device comprising the first and second jaws is positionable adjacent to the retractor.

3. The surgical system of claim 1, wherein:
the first jaw and the second jaw are configured to cut the branch vessel at a cutting point between the first and second jaws and a first distance determined between the cutting point and a first outer edge of the first side, is greater than a second distance, determined between the cutting point and a second outer edge of a second side of the first jaw opposite to the first side.

4. The surgical system of claim 1, wherein the electrode is supported on the first jaw and not the second jaw.

5. The surgical system of claim 1, wherein the electrode is substantially flat and forms a part of the cutting point.

6. The surgical system of claim 1, further comprising:
a lumen in the tube for housing at least a part of an imaging device;
a fluid delivery channel that is fixed in position relative to the tube; and
an opening that is in fluid communication with the fluid delivery channel;
wherein the fluid delivery channel has a first portion and a second portion that forms an angle with an axis of the first portion.

7. The surgical system of claim 6, wherein at least a part of the fluid delivery channel comprises a conduit having a bent configuration.

8. A surgical system, comprising:
a tube having a proximal end and a distal end and a tube axis;
a retractor extendable relative to the distal end of the tube, wherein the retractor is positionable for receiving a main vessel; and
a surgical device separate from the retractor positionable adjacent to and extendable relative to the distal end of the tube, wherein the surgical device comprises a first jaw and a second jaw for grasping tissue through clamping movement of the first jaw with respect to the second jaw by a pivot rotation about a hinge, each of the first and second jaws comprise lateral sides extending generally lengthwise in the direction of the tube, each of the first and second jaws comprising a jaw surface located between the lateral sides, the first and second jaws together forming a jaw assembly, the jaw assembly having a distal end and a proximal region, and further having a concave side and a convex side each extending along a substantial length of the jaw assembly between the proximal region of the jaw assembly and the distal end of the jaw assembly, wherein the first and second jaws pivotably open and close from a first open position to a second position wherein the first and second jaws are closer in proximity to one another in the second position than in the first position, and to a third position wherein the jaw surface of each of the first and second jaws are brought into approximation of each other as opposing surfaces;
a heating element comprised of an electrically conductive material and supported by an electrically insulating surface of the first jaw, the heating element comprising a first heating element terminal and a second heating element terminal for electrically coupling to a first and second terminal of a DC source respectively to provide heat upon receipt of energy from the DC source;
wherein the first jaw comprises a lateral protrusion having an external surface that is electrically insulating, the lateral protrusion is configured for abutting and positioning a main vessel apart from a first portion of an adjoining branch vessel grasped between the first and second jaws, and
wherein the lateral protrusion of the first jaw is spaced apart from the second jaw when the opposing surfaces of the first and second jaws are brought into the third position.

9. The system of claim 8, wherein the first and second jaws form a cavity between the lateral protrusion and the second jaw for minimizing compression of a second portion of the branch vessel positioned within the cavity when the opposing surfaces of the first and second jaws are brought into the third position.

10. The system of claim 8, wherein the lateral protrusion tapers away from the side of the first jaw towards an outer edge of the lateral protrusion.

11. The system of claim 8, wherein the lateral protrusion extends away from the heating element of the first jaw and wherein the heating is asymmetrically positioned relative to the first jaw to minimize thermal spread from the heating element to an outer edge of the lateral protrusion.

12. The system of claim 11, wherein an outer edge of the lateral protrusion is spaced apart from a portion of the heating element by at least about 1 mm.

13. The system of claim 11, wherein the heating element comprises at least two portions spaced apart from one another and electrically communicating with one another.

14. The system of claim 11, wherein the heating element comprises a central portion and two outer portions located on opposing sides of the central portion, wherein the central portion and the two outer portions are spaced apart from one another and electrically communicate with one another, and in cross-section share a rectangular profile along a substantial portion of the first jaw.

15. The system of claim 14, wherein the central portion operates at a higher temperature than either of the two outer portions, and the two outer portions are substantially coplanar with the central portion.

16. The system of claim 8, wherein the second jaw comprises:
a lateral protrusion extending from a side of the second jaw along a lengthwise portion of the second jaw for abutting and positioning the main vessel away from the first portion of the branch vessel grasped between the first and second jaws;
wherein the lateral protrusion of the second jaw is spaced apart from the lateral protrusion of the first jaw when opposing surfaces of the first and second jaws are brought to the third position.

17. The system of claim 16, wherein the lateral protrusion of the second jaw has a tapered configuration.

18. The system of claim 17, wherein the lateral protrusion of second jaw is located opposite to the lateral protrusion of the first jaw and wherein the lateral protrusions of the first and second jaws diverge away from one another.

19. The system of claim 8, wherein the retractor comprises a distal portion slidably extendable from the distal end of the tube, wherein the distal portion of the retractor comprises a first tip and a second tip spaced apart from one another to define a space therebetween for receiving the main vessel.

20. The surgical system of claim 8, wherein the heater element is formed from a single flat substrate.

21. The surgical system of claim 8, wherein the electrically insulating external surface of the lateral protrusion extends from the concave side of the first jaw along a lengthwise portion of the first jaw in a direction that is substantially perpendicular to the tube axis.

22. A surgical system comprising:
a first jaw and a second jaw for grasping tissue, the first and second jaws together forming a jaw assembly that extends generally lengthwise along a first direction, the jaw assembly having a proximal region in which the first and second jaws are connected by a hinge, a distal end, and a jaw assembly length between the distal end and the proximal region, the jaw assembly further having a concave side and a convex side extending between the jaw assembly's distal end and the jaw assembly's proximal region along a portion of the jaw assembly's length, wherein the first and second jaws are located at a distal end of a surgical device and are relatively movable with respect to one another from a first open position, wherein the first and second jaws are spaced apart from one another, to a second closed position wherein the first and second jaws are closer in proximity to one another, and wherein the first and second jaws of the jaw assembly may transition from the first open position to the second closed position by a pivot rotation about the hinge;
wherein each of the first and second jaws comprise an electrically insulating material extending along the length of each of the first and second jaws, the electrically insulating material forming on each of the first and second jaws a lateral protrusion, the lateral protrusions configured for abutting and positioning a main vessel away from a portion of an adjoining branch vessel grasped between the first and second jaws, wherein the lateral protrusions extend laterally from the first jaw and second jaw respectively along the jaw assembly's length in a direction that is generally perpendicular to the first direction, and
wherein the lateral protrusions of the first and second jaws both extend from the concave side, are spaced apart from one another, and form a cavity therebetween for minimizing compression of a second portion of the branch vessel positioned within the cavity when opposing surfaces of the first and second jaws are brought into a position of closest proximity with respect to one another; and
wherein at least one of the opposing surfaces of the first and second jaws supports a heater element made from electrically conductive material and in direct contact with the electrically insulating material of at least one of the first and second jaws.

23. The system of claim 22, wherein the lateral protrusions of the first and second jaws oppose one another and each have a tapered configuration diverging away from one another.

24. The system of claim 22, further comprising a tube capable of receiving the surgical device, wherein the first and second jaws are extendable relative to a distal end of the tube and wherein the system further comprises a retractor that is extendable relative to the distal end of the tube.

25. The surgical system of claim 24, wherein the heater element is formed from a single flat substrate.

26. The surgical system of claim 24, further comprising: a lumen in the tube for housing at least a part of an imaging device; a fluid delivery channel that is fixed in position relative to the tube; and an opening that is in fluid communication with the fluid delivery channel; wherein the fluid delivery channel has a first portion and a second portion that forms an angle with an axis of the first portion.

* * * * *

UNITED STATES PATENT AND TRADEMARK OFFICE
CERTIFICATE OF CORRECTION

PATENT NO. : 9,955,858 B2
APPLICATION NO. : 12/545690
DATED : May 1, 2018
INVENTOR(S) : Ravi Pamnani and Thang Tom Ung It is certified that error appears in the above-identified patent and that said Letters Patent is hereby corrected as shown below:

On the Title Page

(75) replace "Ravi Pamnani" with -- Ravinder D. Pamnani --

Signed and Sealed this
Twenty-fourth Day of May, 2022

Katherine Kelly Vidal
*Director of the United States Patent and Trademark Office*